US009710740B2

(12) United States Patent
Morimoto

(10) Patent No.: US 9,710,740 B2
(45) Date of Patent: Jul. 18, 2017

(54) SYSTEM AND METHOD FOR ARRANGING SHIPMENT AND INSURANCE FOR AN ITEM

(76) Inventor: Nobuyoshi Morimoto, Taipei (TW)

(*) Notice: Subject to any disclaimer, the term of this patent is extended or adjusted under 35 U.S.C. 154(b) by 2795 days.

(21) Appl. No.: 10/045,649

(22) Filed: Nov. 7, 2001

(65) Prior Publication Data

US 2002/0120475 A1 Aug. 29, 2002

Related U.S. Application Data

(63) Continuation-in-part of application No. 09/675,258, filed on Sep. 28, 2000, now Pat. No. 7,035,856, and
(Continued)

(51) Int. Cl.
*G06Q 40/00* (2012.01)
*G06K 17/00* (2006.01)
(Continued)

(52) U.S. Cl.
CPC ....... *G06K 17/0029* (2013.01); *B65D 5/4212* (2013.01); *B65D 23/14* (2013.01); *B65D 25/205* (2013.01); *B65D 79/02* (2013.01); *G06Q 10/0631* (2013.01); *G06Q 10/08* (2013.01); *G06Q 40/08* (2013.01); *A61K 38/00* (2013.01); *B65D 2203/10* (2013.01)

(58) Field of Classification Search
CPC ............... G06Q 40/00; G06Q 50/22
USPC .................................................... 705/4, 2–3
See application file for complete search history.

(56) References Cited

U.S. PATENT DOCUMENTS 4,799,156 A 1/1989 Shavit et al.
4,831,526 A * 5/1989 Luchs et al. .................. 705/4
(Continued)

FOREIGN PATENT DOCUMENTS

DE 44 46 203 6/1996
DE 44 46 203 A1 * 6/1996
(Continued)

OTHER PUBLICATIONS eHealthInsurance @ http://web.archive.org/web/http://www.eHealthInsurance.com. Copyright 1998-2000.*
(Continued)

*Primary Examiner* — Robert Sorey
*Assistant Examiner* — Kristine Rapillo
(74) *Attorney, Agent, or Firm* — Robert C. Kowert; Meyertons, Hood, Kivlin, Kowert & Goetzel, P.C.

(57) ABSTRACT

A system and method for arranging shipment and insurance for items being shipped in containers with memory devices. An intelligent shipping agent may receive a request to ship an item. The intelligent shipping agent may search a database or solicit quotations to obtain shipping and insurance services for an item to be shipped from an origination to a final destination. The intelligent agent may find an entry in the database or may select a vendor based on received quotations. The selection may maximize value of a product or service at the lowest cost. The memory device may store shipping and insurance information related to the item being shipped in a data file. The memory device may include input devices and sensors to gather and store information before, during and after shipment.

20 Claims, 16 Drawing Sheets

Related U.S. Application Data a continuation-in-part of application No. 09/675,264, filed on Sep. 28, 2000, now abandoned.

(60) Provisional application No. 60/247,272, filed on Nov. 10, 2000.

(51) Int. Cl.
*B65D 5/42* (2006.01)
*B65D 23/14* (2006.01)
*B65D 25/20* (2006.01)
*B65D 79/02* (2006.01)
*G06Q 10/06* (2012.01)
*G06Q 10/08* (2012.01)
*G06Q 40/08* (2012.01)
*A61K 38/00* (2006.01)

(56) References Cited

U.S. PATENT DOCUMENTS

| | | | |
|---|---|---|---|
| 5,015,145 A | 5/1991 | Angell et al. | |
| 5,038,283 A | 8/1991 | Caveney | |
| 5,063,506 A | 11/1991 | Brockwell et al. | |
| 5,117,096 A | 5/1992 | Bauer et al. | |
| 5,123,541 A | 6/1992 | Gianni et al. | |
| 5,261,282 A | 11/1993 | Grabowski et al. | |
| 5,347,845 A * | 9/1994 | Kepler | G01M 3/205 209/552 |
| 5,413,236 A | 5/1995 | Kenevan | |
| 5,466,030 A | 11/1995 | Harris et al. | |
| 5,504,674 A * | 4/1996 | Chen et al. | 705/4 |
| 5,522,471 A | 6/1996 | Hilgendorf | |
| 5,565,858 A | 10/1996 | Guthrie | |
| 5,610,344 A * | 3/1997 | Ueda et al. | 73/865.6 |
| 5,627,517 A * | 5/1997 | Theimer | G01S 13/78 340/426.2 |
| 5,666,493 A | 9/1997 | Wojcik et al. | |
| 5,686,888 A * | 11/1997 | Welles, II | B61L 25/025 340/3.31 |
| 5,712,788 A | 1/1998 | Liaw et al. | |
| 5,715,398 A | 2/1998 | Lubenow et al. | |
| 5,765,707 A | 6/1998 | Kenevan | |
| 5,804,810 A * | 9/1998 | Woolley | G01S 5/0289 235/375 |
| 5,949,876 A | 9/1999 | Ginter et al. | |
| 5,959,568 A | 9/1999 | Woolley | |
| 6,047,273 A * | 4/2000 | Vaghi | G06F 21/629 705/401 |
| 6,099,047 A | 8/2000 | Reiff et al. | |
| 6,115,695 A | 9/2000 | Kern | |
| 6,128,549 A | 10/2000 | Swartz et al. | |
| 6,151,582 A | 11/2000 | Huang et al. | |
| 6,199,046 B1 | 3/2001 | Heinzle et al. | |
| 6,233,568 B1 * | 5/2001 | Kara | G01G 19/005 705/401 |
| 6,236,971 B1 | 5/2001 | Stefik et al. | |
| 6,285,916 B1 * | 9/2001 | Kadaba et al. | 700/222 |
| 6,321,992 B1 | 11/2001 | Knowles et al. | |
| 6,332,098 B2 | 12/2001 | Ross et al. | |
| 6,344,794 B1 * | 2/2002 | Ulrich et al. | 340/539.16 |
| 6,356,802 B1 | 3/2002 | Takehara et al. | |
| 6,370,222 B1 * | 4/2002 | Cornick, Jr. | G01V 5/0016 378/57 |
| 6,398,109 B1 | 6/2002 | Ohki | |
| 6,429,810 B1 | 8/2002 | De Roche | |
| 6,460,020 B1 | 10/2002 | Pool et al. | |
| 6,934,692 B1 * | 8/2005 | Duncan | G06Q 20/10 705/14.4 |
| 7,117,170 B1 * | 10/2006 | Bennett | G06Q 10/08 705/34 |
| 2001/0042055 A1 * | 11/2001 | Didriksen et al. | 705/407 |
| 2001/0043273 A1 | 11/2001 | Herrod et al. | |
| 2002/0107785 A1 * | 8/2002 | Melchior et al. | 705/37 |
| 2002/0116228 A1 * | 8/2002 | Bauer et al. | 705/4 |
| 2002/0156656 A1 * | 10/2002 | Harrell | G06Q 30/00 705/4 |
| 2002/0198744 A1 * | 12/2002 | Sagalow et al. | 705/4 |
| 2003/0101106 A1 * | 5/2003 | Mizushima et al. | 705/28 |
| 2003/0183697 A1 | 10/2003 | Porter | |

FOREIGN PATENT DOCUMENTS

| | | | |
|---|---|---|---|
| DE | 198 13 842 | 9/1999 | |
| JP | 5-242106 | 9/1993 | |
| JP | 2001-171811 | 6/2001 | |
| JP | 2001-253517 | 9/2001 | |
| WO | 96/13015 | 5/1996 | |
| WO | 99/23623 | 5/1999 | |
| WO | WO 02/19046 * | 3/2000 | G05B 19/05 |
| WO | WO 01/39090 * | 5/2001 | G06F 17/60 |
| WO | WO 0139090 A1 * | 5/2001 | G06Q 40/08 |
| WO | WO 0219046 A1 * | 3/2002 | G06Q 10/047 |

OTHER PUBLICATIONS

Hubbard, C. T. "Registered Mail Transit Insurance" Dec. 27, 1943. Barron's National Business and Financial Weekly. vol. 23, Iss. 52. p. 20.*
Business Wire. "WebTradeInsure First to Provide Comprehensive e-Marketplace Internet Fraud Protection Services for Online Auction and Business Exchange Transactions" Jul. 11, 2000. p. 1.*
Thurston, Scott. "UPS sued over fee for parcel insurance" Nov. 20, 1999. The Atlanta Journal The Atlanta Consitution. p. D.1.*
PR Newswire. "Global Souces and dollarDEX Establish Online Cargo Insurance Services" Sep. 28, 2000. p. 1.*
PR Newswire. "E-Stamp Corporation Announces Aggressive Strategy for Growth" May 12, 2000. p. 1.*
Rucker, John. "Recognize Your Risks" Nov. 1994. Transportation & Distribution. vol. 35, Iss. 11. p. 55.*
Hickey, Kathleen. "Internet Care" Jul. 17, 2000. Journal of Commerce. p. 23.*
Strazewski, Len. "Picture This" Sep. 2000. Rough Notes. vol. 143, Iss. 9. p. 108.*
Anonymous. "A picture is worth a thousand dollars" Feb. 1994. Distribution. vol. 93, Iss. 2. p. 12.*
UPS @ http://web.archive.org/web/20000818221434/http://ups.com/idex.html. Copyright 1994-2000.*
U-PIC @ http://web.archive.org/web/20000711033858/http://www.u-pic.com/. Copyright 1999.*
Pipinsure @ http://web.archive.org/web/20000619183651/http://www.pipinsure.com/welcome.html. Copyright 2000.*
eBay @ http://web.archive.org/web/19991110180343/http://www.eBay.com/index.html. Copyright 1995-1999.*
http://web.archive.org/web/20000619183651/http://www.pipinsure.com/welcome.html.*
"MSR Visual Exporter: Premium Global Export Software," 6 pgs., © 2001 MSR International, Inc.
Kumar, et al., "Building the 'last mile'—how to solve logistics conflicts in e-business," © European Business Forum Limited 2000, pp. 66-70.
"Yusen Air & Sea Services USA), Inc.," © 2001 Yusen Air & Sea Service Co., Ltd., pp. 1-6.
"FedEx Tracking," © 1995-2001 FedEx, pp. 1-2.
"UPS Handheld Solutions," © 1994-2000 United Parcel Service of America, Inc. pp. 1-2.
"UPS Shipping and Tracking Solutions," © 1994-2000 United Parcel Service of America, Inc. pp. 1-4.
"UPS OnLine WorldShip," © 1994-2000 United Parcel Service of America, Inc. pp. 1-4.
"UPS OnLine Host Access," © 1994-2000 United Parcel Service of America, Inc. pp. 1-2.
"UPS OnLine Compatible Solutions," © 1994-2000 United Parcel Service of America, Inc. pp. 1-4.
"Intrepa Products & Services," © 2000 Intrepa LLC, pp. 1-3.
"Shipment Packaging Software from Cargoware," © 1999 Cargoware, pp. 1-2.
Stenmark, "Information Agents for the Web," Feb. 1998, 2 pages.

(56) References Cited

OTHER PUBLICATIONS

The gadgeteer, "Earthmate GPS Review," by Julie on Feb. 1, 1999, downloaded from http://the-gadgeteer.com/1999/02/01/earthmate_gps_review/[Apr. 30, 2012 12:34:08 PM], 8 pages.
D. Ellis, "GPS-NAV Version 6.0—User's Guide Update," Mar. 22, 2000, 3 pages, downloaded from http://www.cambridge-aero.com/manuals/GPSV6insertE.pdf.
Gadget Central, Inc., "The Pilot's never lost . . . GPS Module for lost Palm "Pilots"", Apr. 29, 2000, downloaded from http://www.gadgetcentral.com/rand_palm_intro.htm[Apr. 30, 2012 10:29:09 AM].

\* cited by examiner

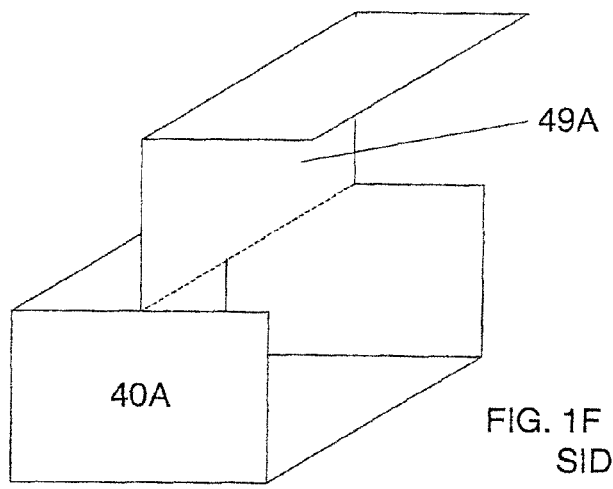
FIG. 1F (OPEN SIDE)
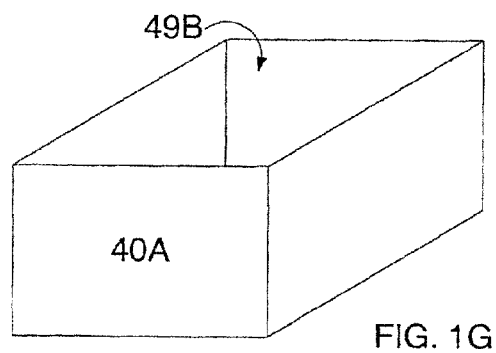
FIG. 1G (OPEN TOP)
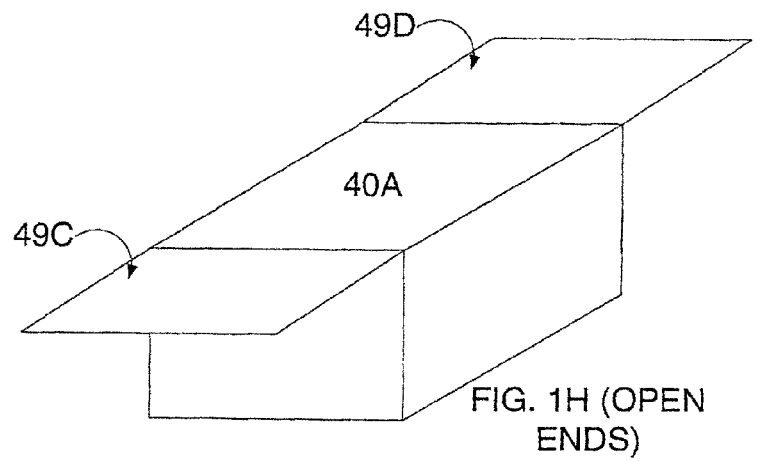
FIG. 1H (OPEN ENDS)

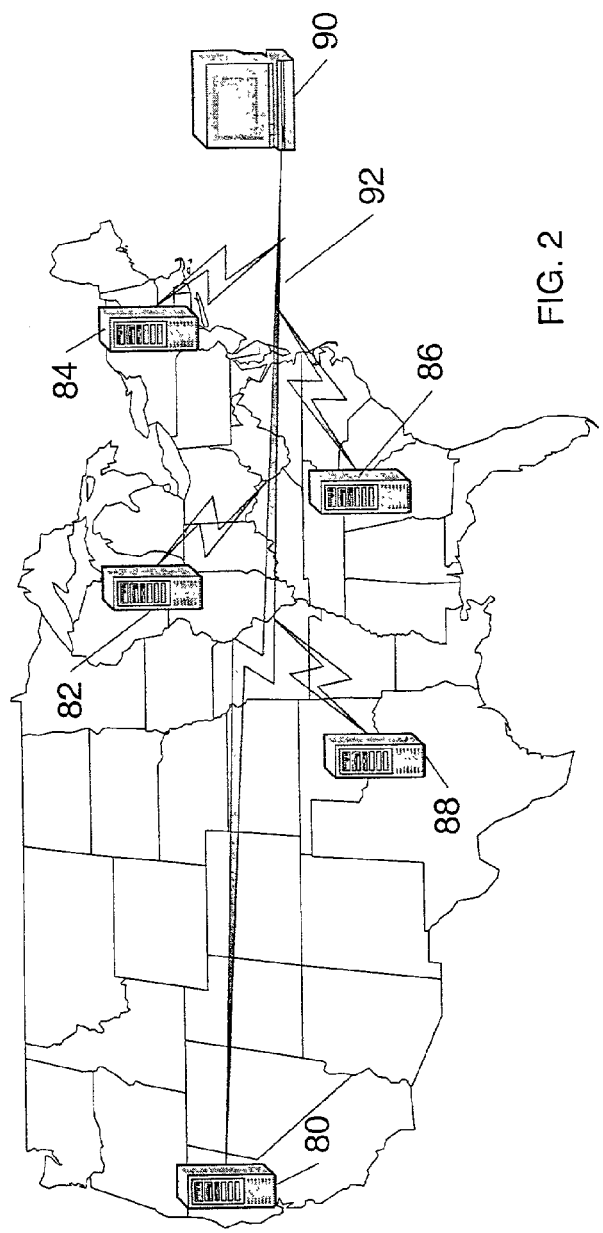
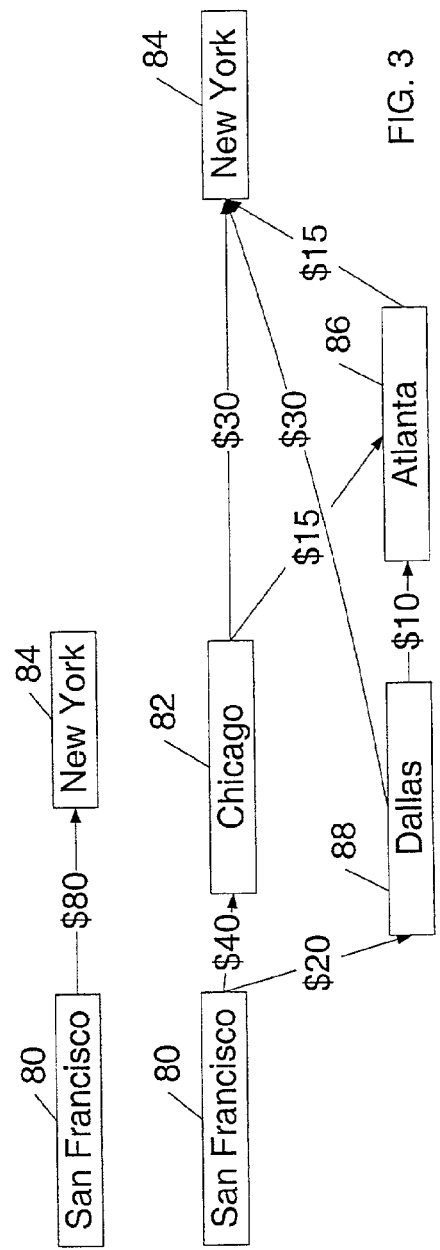

50A

| | |
|---|---|
| Package/Item Tracking No. | |
| Description of Goods | |
| Weight | |
| Special Shipping Information (e.g., temperature restrictions) | |
| Insurance amount, terms (e.g., deductible) | |
| Ship Date | Arrival Deadline |
| Origination | Destination |
| Payment Terms | |
| Sender's Name | Sender's e-mail address |
| Sender's telephone | Sender's street address |
| Sender's Account Number | |
| Recipient's Name | Recipient's e-mail address |
| Recipient's telephone | Recipient's street address |
| Recipient's Account Number | |
| 1st Intermediate Destination | |
| 1st Intermediate Destination Arrival Date | |
| 1st Intermediate Destination Ship Date | |
| 1st Intermediate Destination Shipper Info | |
| 2nd Intermediate Destination | |
| 2nd Intermediate Destination Arrival Date | |
| 2nd Intermediate Destination Ship Date | |
| 2nd Intermediate Destination Shipper Info | |
| 3rd Intermediate Destination | |
| 3rd Intermediate Destination Arrival Date | |
| 3rd Intermediate Destination Ship Date | |
| 3rd Intermediate Destination Shipper Info | |

FIG. 4

SYSTEM AND METHOD FOR ARRANGING SHIPMENT AND INSURANCE FOR AN ITEM

PRIORITY INFORMATION

This application claims the benefit of priority from U.S. Provisional Application No. 60/247,272, filed Nov. 10, 2000. This application is a continuation-in-part of U.S. application Ser. No. 09/675,258, filed Sep. 28, 2000. This application is also a continuation-in-part of U.S. application Ser. No. 09/675,264, filed Sep. 28, 2000.

BACKGROUND OF THE INVENTION

1. Field of the Invention

The present invention generally relates to the shipping or mailing of items from one place to another. More particularly, the present invention relates to a system and method for arranging shipment and insurance for an item that is being shipped or mailed.

2. Description of the Related Art

Internet commerce has become an increasingly popular form of commerce in the United States and throughout the world. In general, Internet-based commerce, often referred to as e-commerce, provides advantages to both suppliers and consumers. E-commerce provides vendors and service providers the ability to greatly increase their sales channel and distribution network with minimal cost. An Internet commerce site provides a convenient, effective and secure mechanism for potential buyers to browse, select and purchase goods or services in an easy and simple fashion.

However, Internet retailers face many obstacles to turning a profit. Chief among these obstacles are high shipping costs. For example, assuming an online retailer of compact disks (CDs) based in California sells a CD to a customer in New York for $12. The customer may be unwilling to pay $3 (i.e., 25% of the sales price) for shipping. Internet retailers of consumer goods such as CDs, videos, and consumables face a more difficult challenge than retailers of more expensive items such as jewelry. Consumers are less likely to object to paying a $3 shipping charge for a $100 necklace than for a $12 CD.

Taxes combine with shipping costs to influence online consumer purchasing decisions. Currently, many Internet retailers do not charge their customers sales tax, which tends to offset the high shipping costs to some extent. However, sales tax is typically less than 10% of the sales price, so shipping costs still pressure Internet retailers to lower their prices more than traditional brick-and-mortar retail stores. Furthermore, the future of current moratoriums on Internet sales taxes remains uncertain. It is likely that traditional brick-and-mortar retailers will exert considerable pressure on federal and state governments to "even the playing field" by forcing Internet retailers to pay some sort of Internet sales tax. For this reason, the importance of reducing shipping costs may become even more critical in the near future. Of course, reduced shipping costs may also benefit non-Internet businesses and consumers in general.

Many consumers also regard the insurance costs as being too high, further adding to the overall cost of the product. This is especially true when the shipping and insurance costs account for a substantial percentage of the product costs. For example, many consumers may object to paying $3 in shipping charges and $1 for insurance costs when they purchase a $12 music CD. Thus, an improved system and method for arranging shipment and insurance for an item that is being shipped or mailed is needed.

SUMMARY OF THE INVENTION

The problems outlined above may at least in part be solved by an improved system and method for arranging shipment and insurance for an item that is being shipped or mailed. An intelligent shipping agent may receive a request from a client to ship an item from an origination point to a destination point.

In one embodiment, the intelligent shipping agent may search a database to find one or more suppliers offering the highest value for the lowest cost. The intelligent agent may periodically gather information related to shipment and insurance from suppliers and store and/or update the information in the database. In one embodiment, the intelligent agent may solicit quotations from two or more suppliers of shipping and insurance service providers to obtain shipping and insurance services for an item to be shipped from an origination to a final destination. In one embodiment, the intelligent agent may solicit quotations from providers of such service over the Internet. A finite time may be specified for receiving the responses from the providers.

In one embodiment, the intelligent agent may find an entry in the database, which provides the item to be shipped and/or insured for the lowest cost. In one embodiment, the intelligent shipping agent may select a vendor for shipping and/or insurance services based on the received quotations. The selection method may seek to maximize the value of a product or service at the lowest cost. The intelligent agent may send a confirmation to the selected vendor to provide the requested shipping and/or insurance service.

The memory device may store shipping and insurance information related to the item being shipped in a data file. The memory device may include input devices and sensors to gather and store information before, during and after shipment. The data file may be updated to reflect the changes. A system for arranging shipment and insurance for an item being shipped is also contemplated. The system performing the function of an intelligent shipping agent, i.e., an intelligent shipping agent system may include the memory device communicating with a central server. The central server may host software to perform the intelligent shipping agent function. The communication may occur over a network. In one embodiment, the system may also include hand-held communicating device, with a display device, that allows the user to easily view the contents of the memory device. The hand-held device may also have an input device (e.g., a set of buttons or an entire keyboard) that allows the user to append and edit information for storage in the memory device. The hand-held device may also include a network interface configured to allow the hand-held device to send and receive information from a computer network (e.g., the Internet). In one embodiment, the memory device may communicate directly with the central server. The memory device may also include sensors configured to capture information about the carriers, containers and/or items. For example, the sensor may include a scale configured to store the weight of the carrier/container/item. The sensor may also include a digital camera configured to capture digital images of the carrier/container/item. The weight and images may be useful for customs purposes and to prove the condition of the item being shipped. The system may be configured to transmit information from the sensors using the computer network, or to store the information in the memory device.

In one embodiment, the system may be configured to interface with the memory device (e.g., using a wireless link) and read the memory device to determine the best routing for the item to be shipped. The system may be hand-held or built into a stationary apparatus such as a conveyer belt or an automated loading and unloading station. The system may also include a scale to weigh the item in the container, and one or more digital cameras to capture images of the container and item. The system may include a database to store and update the data file.

The containers and/or carriers may have attached or embedded memory devices for storing information about the item(s) being shipped. This may advantageously simplify the process of transferring the carriers since the memory device may store the routing and final destination of the container/carrier, as well as other information such as: contact information for each shipping company that will handle the container, contact information for the person or company that originally sent the item, contact information for the person or company that is to be the final recipient of the item, a description of the item (so that the container does not have to be opened to identify its contents), a unique identifier (e.g., a container or shipping tracking number), any special handling requirements, the weight of the container, customs information, and insurance information.

In one embodiment, the memory device may be configured with a wireless interface (e.g., infrared or radio wave) that allows the contents of the memory device to be read and updated without physically contacting the device. This may simplify the transfer of the container at intermediate destinations, and may also allow the information stored in the memory device to be updated as the container progresses through its designated routing. For example, at each intermediate destination, the shipping company may update the information in the memory device to reflect the time that the container was received. Other information may also be updated (e.g., the condition of the container and/or item). In some embodiments, the memory device may be attached to the item itself.

BRIEF DESCRIPTION OF THE DRAWINGS

The foregoing, as well as other objects, features, and advantages of this invention may be more completely understood by reference to the following detailed description when read together with the accompanying drawings in which:

FIGS. 1F-H illustrate details of different embodiments of the container from FIG. 1A;

FIG. 2 illustrates one embodiment of a network of regional shipping locations, hubs, or transfer points;

FIG. 3 illustrates how an indirect shipping route with one or more intermediate destinations may be less expensive than a direct shipping route;

FIG. 4 illustrates one embodiment of a data file that may be stored in a memory device attached to a container or carrier for shipping packages;

Figure 1A:
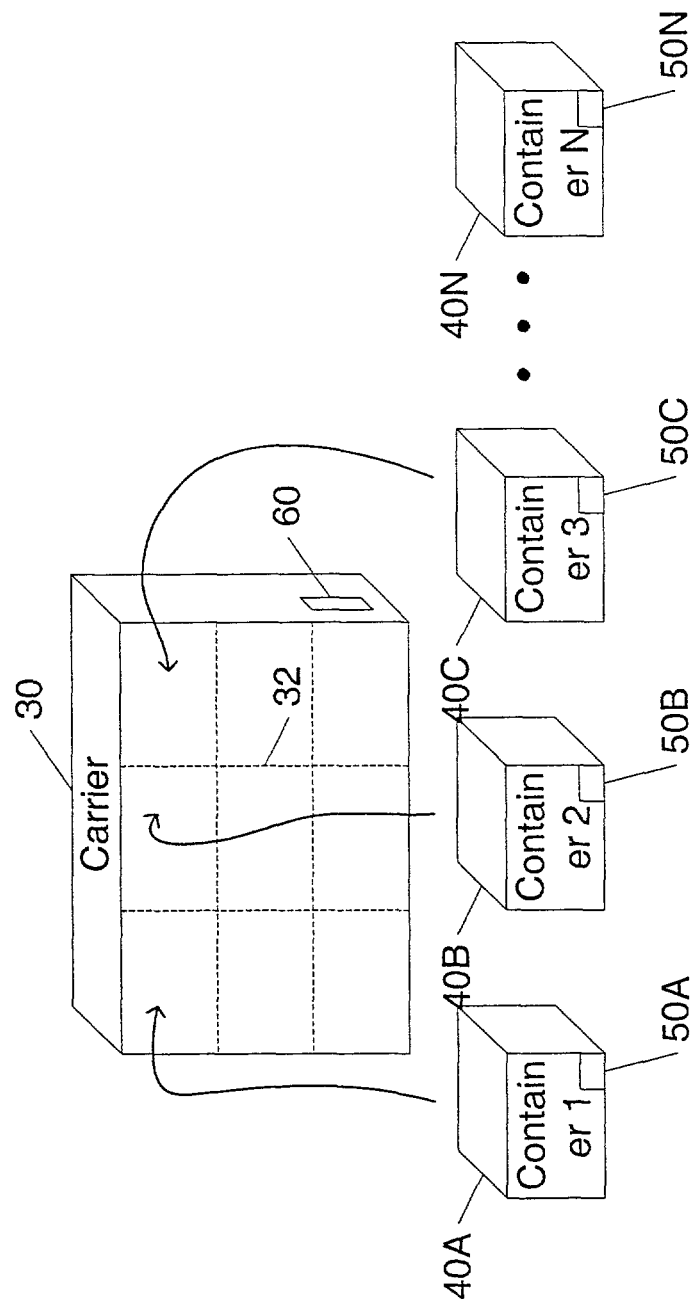
FIG. 1A illustrates one embodiment of a container and carrier system for efficiently transporting goods.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims.

Please note that the headings used herein are for organizational purposes only and are not meant to limit the description or claims. Further note that as used herein, the terms "package", "goods", and "item" are used interchangeably to refer to an item being shipped. Also note, the word "may" is used in this application in a permissive sense (i.e., having the potential to, being able to), not a mandatory sense (i.e., must). As used herein, the terms "ship" and "shipping" shall include all types of conveyance, including using express carriers (e.g., Federal Express, Airborne, DHL), postal or parcel carrier services (e.g., the United States Postal Service and United Parcel Service), local delivery services (e.g., bicycle, motorcycle, car) and freight carriers (e.g., air, rail, ship, and truck).

DETAILED DESCRIPTION OF SEVERAL EMBODIMENTS

FIGS. 1A-K: Carrier and Containers

Turning now to FIG. 1A, one embodiment of a carrier 30 configured to allow efficient shipping of goods is shown. In this embodiment, carrier 30 is configured to store a number of individual containers 40A through 40N. Carrier 30 may be configured to allow each individual container to be inserted or removed on an individual basis. Carrier 30 may be configured with a memory 60 that is configured to store electronic data. Similarly, containers 40A through 40N may also be configured with memory devices 50A through 50N, respectively. Memory 60 may be configured to store various information corresponding to carrier 30 (and possibly containers 40A-N stored within carrier 30). Similarly, memory devices 50A through 50N may be configured to store electronic data corresponding to containers 40A through 40N, respectively. Carrier 30 may be constructed of a number of different materials, including plastic, wood, or aluminum. Carrier 30 may be configured with an internal frame 32 that allows containers 40A-N to be inserted securely within carrier 30. Frame 32 may advantageously prevent containers from shifting during shipping, e.g., if carrier 30 is not completely full of containers. Frame 32 may also include tracks or shelves with rollers that allow each container within the carrier to be inserted and removed more easily. While containers 40A-N are preferably the same size, in some configurations different container sizes may be made available for larger items to be shipped. For example, each standard container may be 0.5 m by 0.5 m by 1.5 m, with nine containers fitting in carrier 30 in a 3 by 3 configuration. However, a larger container measuring 1.0 m by 1.0 m by 1.5 m may be used for oversized items. This larger container may fit within carrier 30 with up to five of the standard containers. Other configurations and sizes are also possible and contemplated (e.g., a 3×3×2 arrangement of containers within carrier 30, or containers measuring 20 feet by 40 feet). The containers may be configured to meet industry standard requirements such as strength, resilience, durability, and a lack of hidden compartments (i.e., to address smuggling concerns).

In one embodiment, memory 60 may be configured to store a unique item identification number (e.g., a serial number) for carrier 30. Memory 60 may also be configured to store origination information and final destination information for carrier 30. For example, carrier 30 may be shipped from Tokyo to New York, and memory 60 may be configured to store that information. Various additional information may also be stored in memory 60 (e.g., container identification numbers for each container stored within carrier 30). If carrier 30 is shipped to one or more intermediate destinations (e.g., from Tokyo to New York via Chicago), then information regarding the intermediate destination may also be stored in memory 60. Other information about carrier 30 (and containers 40A-N within carrier 30) may also be stored in memory 60. For example, the contents of each container 40A-N may be stored in memory 60. Insurance and customs information may also be stored in memory 60.

Memory devices 50A-N may be configured similarly to memory device 60. For example, in one embodiment memory device 50A may be configured to store origination information, intermediate destination information, and final destination information for container 40A. Memory device 50B may store similar information for container 40B. The memory devices may be implemented using a number of different technologies (e.g., Flash memory, SRAM, DRAM, EEPROM, hard drive, removable optical or magnetic media). The memory devices may have a power supply (e.g., a battery, solar panel, or both) connected to it (e.g., in the case of DRAM), or it may rely on the power supply of the processing unit at the shipping location to provide the necessary power to perform reads and writes. The memory devices may also include interface logic (e.g., transceivers and memory controllers) and appropriate connectors (e.g., RS-232 or universal serial bus (USB)) to control the read and write process. In some embodiments, the memory devices may further include a wireless interface (e.g., infrared or radio wave) to allow the contents of the memory devices to read and written to without requiring a physical connection to the device.

In yet another embodiment, barcode stickers may be used as a memory device. In this embodiment, the barcode may be printed out on a sticker and subsequently affixed to the container and/or carrier. Additional data may be printed out on additional stickers and affixed to the container and/or carrier near the previous sticker. The information may be read by a barcode scanner which is configured to read all of the barcodes affixed on the carrier or container. In one embodiment, the barcode may be interfaced with a solar-powered energy-saving barcode reader to retrieve data about the container. In the event that some of the data needs to be overwritten, additional barcode stickers may be printed out and affixed to the container or carrier over the preceding barcode stickers. Advantageously, this may provide an inexpensive read-write memory device.

Depending on the embodiment, however, the memory device need not be physically attached to the container or carrier. For example, the memory device may be implemented as a small electronic component (e.g., encased in plastic) designed to be packed inside the container with the goods being shipped.

In embodiments that utilize active memory devices (e.g., electronic or magnetic memory as opposed to barcodes, which are a passive memory), additional features such as global positioning and environmental (e.g., temperature, humidity, vibration, sound, light, air contaminants) sensors may also be implemented as part of the memory devices. For example, the memory device for a particular container may include a microprocessor (or microcontroller) and a temperature sensor. The microprocessor may be configured to periodically sample the temperature readings from the sensor. If the temperature exceeds a predetermined threshold (e.g., too low or too high), then the processor may store an indication of this (e.g., the exact temperature and the time that the event took place) in the memory device. Alternatively, the processor may be configured to store all periodic temperature readings in the memory device, thereby providing the recipient and the shipping company with a complete log of the temperatures experienced by the container throughout the shipping process. Taking the wireless connection one step further, the memory device may be configured with a long-range wireless communications device (e.g., with a cellular or PCS telephone link, satellite link, or other wireless network protocol) to allow the memory device to periodically upload the temperature information and the data file to central server 90. In embodiments where the memory device includes other environmental sensors, other environmental data may be recorded in the memory device and/or transmitted via a wireless link. In one embodiment, central server 90 may be included in an intelligent shipping agent system. An intelligent shipping agent may be implemented in software configured to execute on a system of one or more computers coupled by a network. The software may be configured to arrange shipment and insurance for items being shipped or mailed.

Other possibilities include an optional GPS (global positioning system) sensor that can store position information for the container. Currently, the cost of long-range wireless communications and GPS sensors may be prohibitive, but if prices continue to drop, these may become more economical options. The memory device may also store digital images of the items being shipped (e.g., as the items are being packed to prove that the items are in good condition before shipment). An insurance company may use shipped item information, such as digital images stored in the memory device, to settle damage claims filed by a sender and/or a receiver.

Advantageously, the configuration of carrier 30 and containers 40A-N shown in the figure may allow for arranging shipment and insurance for items being shipped. For example, regional shipping companies may make arrangements to have a carrier such as carrier 30 routinely shipped on certain flights from a particular origination to a particular destination (e.g., from San Francisco to Dallas, and from Dallas to New York). A regional shipping company based in San Francisco may make arrangements with one or more airlines so that the airlines will carry one carrier from San Francisco to Dallas per day. Similarly, a carrier based in New York may make a similar arrangement with one or more airlines to carry a carrier from Dallas to New York on a daily basis. As noted above, this type of shipping arrangement may advantageously result in lower shipping costs. If each regional shipping company uses a standard carrier (e.g., carrier 30) and standard containers (e.g., containers 40A through N), then a customer having one or more containers to be shipped from San Francisco to New York may be able to have the containers inserted into the first shipping company's carrier going from San Francisco to Dallas, and then have the containers transferred to the second carrier going from Dallas to New York. In some cases, this routing may be cheaper than a direct routing from San Francisco to New York.

In some embodiments, this method for shipping may be analogized to the packet switching performed in IP or telephone networks. In a traditional telephone system, a dedicated circuit was established between the caller and recipient for each call. This mirrors traditional shipping in which a customer makes an arrangement with a single shipping company for shipment of an item from an origination point to a final destination. However, in recent years the telephone company digitizes the voice at either end of a telephone call and breaks the information into packets. These packets are then routed individually from the origination to the destination. For a single call, one packet might be routed through Chicago, while the following packet may be routed through Dallas. Similarly, a customer having to ship twelve containers from San Francisco to New York may find a better price by breaking up the container shipments and routing the containers individually. Some containers may take a direct flight from San Francisco to New York, while others may be routed through Dallas or Chicago.

Advantageously, memory devices 50A-N and 60 may simplify the transfer of containers at intermediate destinations such as Dallas or Chicago in the example above. As noted above, in some embodiments each memory device may include a wireless transceiver configured to send and receive information to a processing unit. The processing unit may be used by the shipping company personnel at the intermediate destination to rapidly determine which containers need to be removed from which carriers, and which new carriers the containers should be inserted into.

Figure 1B:
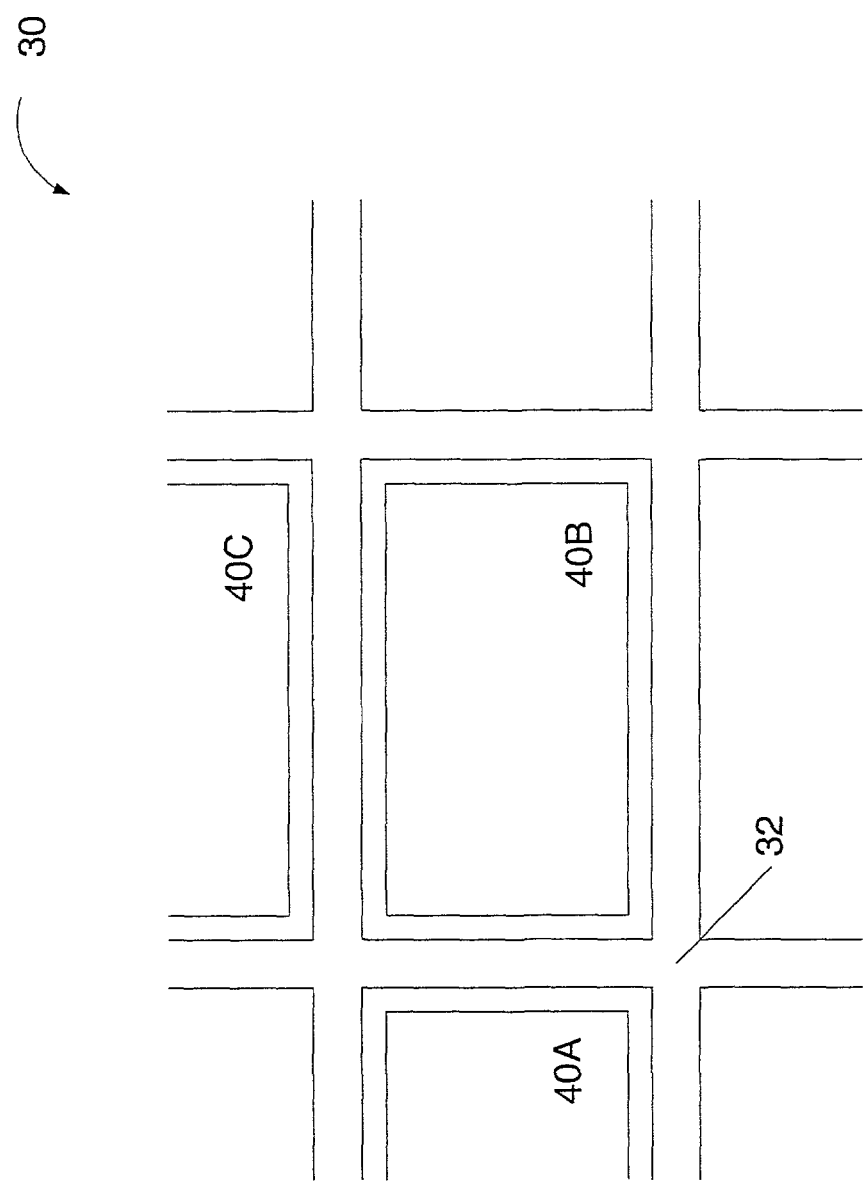
FIG. 1B illustrates a close-up view of one embodiment of the container and carrier system from FIG. 1A.

Turning now to FIG. 1B, details of one embodiment of carrier 30 are shown. In this embodiment, containers 40A-C are configured to slide into carrier 32, and carrier 32 is configured to protect and secure each container 40A-C, even if the carrier is not completely full. As shown in the figure, carrier 30 may be formed as a rigid frame spaced so as to allow containers to be inserted and removed on an individual basis. Carrier 30 may be made of any suitable material, e.g., plastic, aluminum, carbon fiber, fiberglass, wood, or a combination thereof.

Figure 1C:
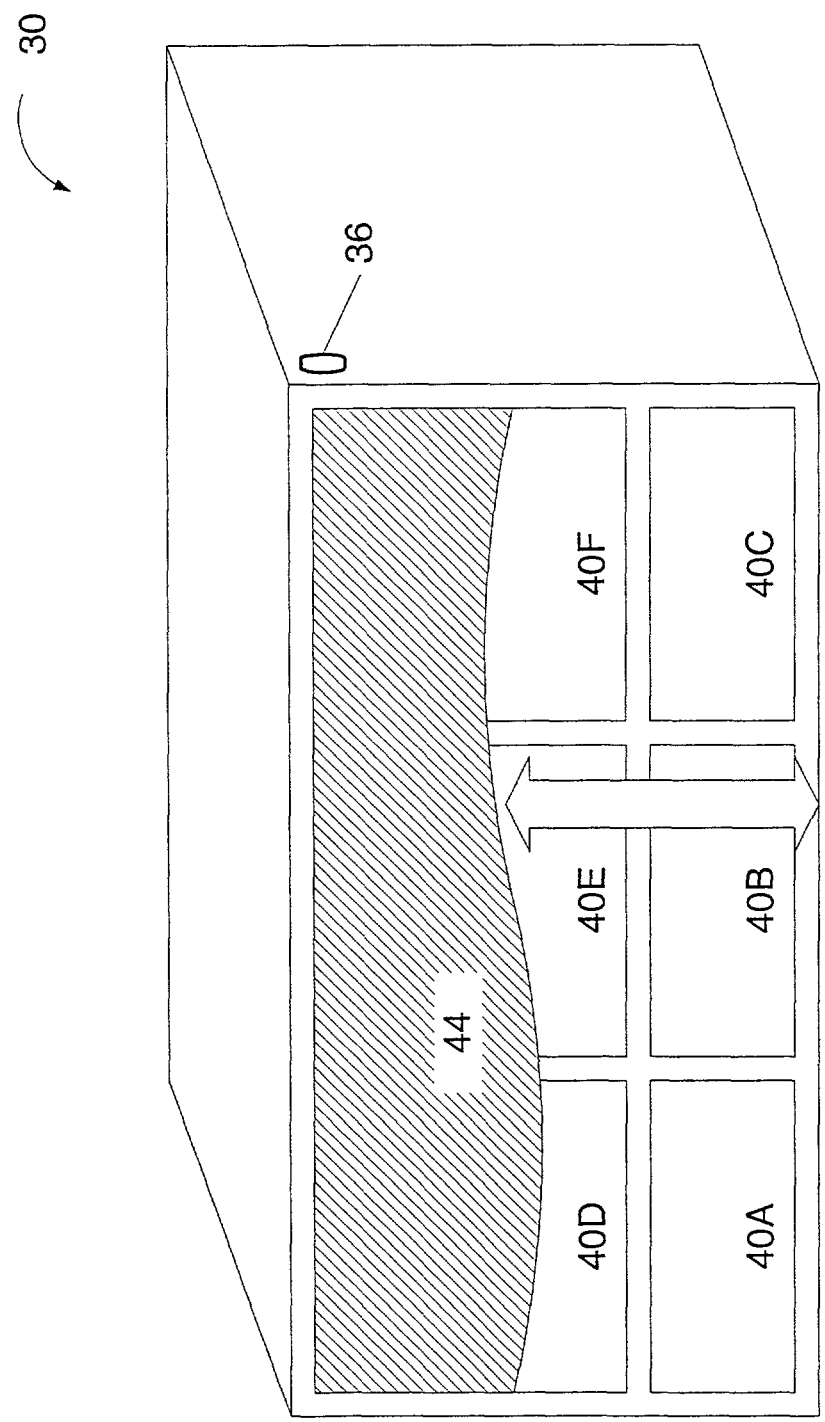
FIGS. 1C-E illustrate details of different embodiments of the container and carrier system from FIG. 1A.

Turning now to FIG. 1C, another embodiment of carrier 30 is shown. In this embodiment, carrier 30 includes a cover 44 and a rotating spool mechanism 36 that is configured to raise and lower cover 44. In some embodiments the cover may be raised and lowered manually (e.g., using a manual crank arm that is connected to spool mechanism 36). In other embodiments, spool mechanism may be an electric motor that is configured to automatically raise or lower cover 44. An internal battery may be included within carrier 30, or an external power source may be connected to spool mechanism 36. Cover 44 may be of any suitable material (e.g., cloth, nylon mesh, chain mesh) that prevents containers 40A-N from falling out of or being removed from carrier 30. Cover 44 may have a locking mechanism (e.g., a combination or a key lock) that prevents unauthorized handlers from removing or accessing containers in carrier 30.

Figure 1D:
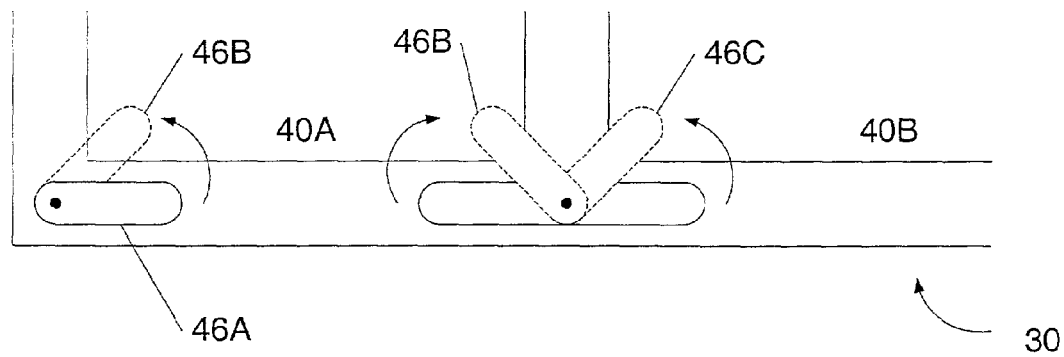

Turning now to FIG. 1D, details of a portion of one embodiment of carrier 30 are shown. In this embodiment, carrier 30 includes locking clips 46A-C which are coupled to carrier 30 in a moveable fashion. Locking clips 46A-C may be positioned either to allow the corresponding container (e.g., containers 40A and 40B) to be inserted or removed from carrier 30, or to prevent the containers from being removed. As with cover 44 in the previous embodiment, locking clips 46A-C may be configured to require a key or combination to prevent unauthorized removal or tampering.

Figure 1E:
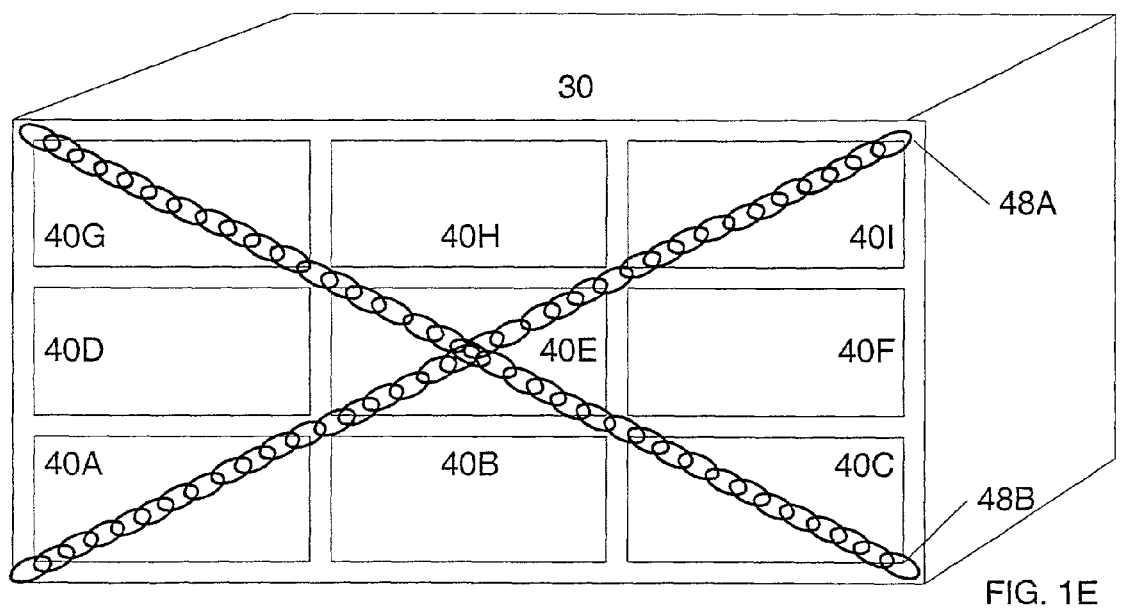

Turning now to FIG. 1E, another embodiment of carrier 30 is shown. In this embodiment, carrier 30 includes chains 48A-B that are configured to secure containers 40A-I into carrier 30. While a number of different configurations for carrier 30 have been described herein, other configurations are possible and contemplated. For example, combinations of locking clips 46A-C, chains 48A-B, and cover 44 may be used. Other fastening devices such as latches and lids that are configured to be bolted onto carrier 30 may also be used in addition to, or in lieu of, the configurations described above.

Turning now to FIGS. 1F-1H, a number of different configurations of container 40A are shown. Container 40A may be configured with a hinged top and side 49A, an open top 49B, or hinged sides 49C-D. The exact configuration of container 40A may vary based on the type of items being shipped or the configuration of carrier 30.

Figure 1J:
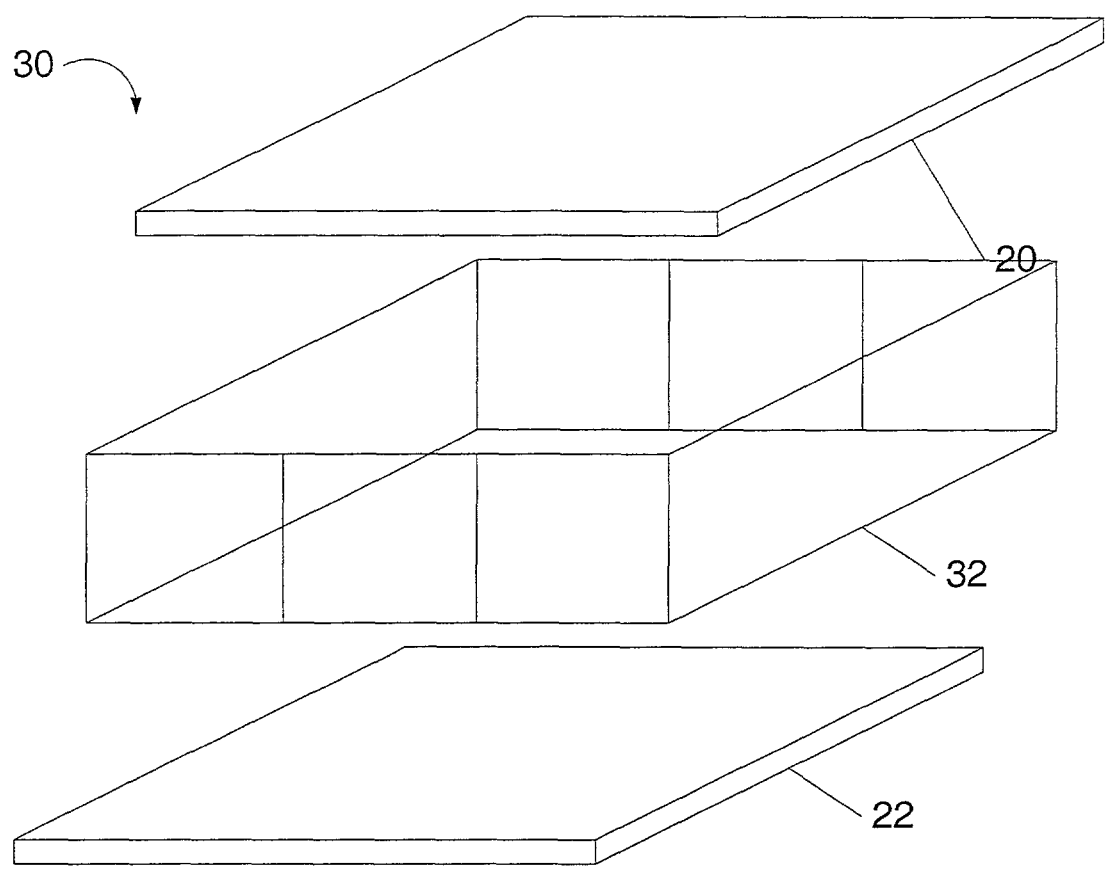
FIG. 1J illustrates one method for constructing the carrier system from FIG. 1A.

Turning now to FIG. 1J, one possible method for constructing carrier 30 is shown. In this embodiment, carrier 30 comprises a rigid frame 32 (e.g., constructed of metal such as aluminum) that provides strength to prevent compression damage, and top and bottom members 20-22, which provide additional strength to prevent bending or twisting of frame 32 or containers within frame 32. Top and bottom members 20-22 may be constructed of materials such as wood, plastic, fiberglass, or aluminum. Additional sides may also be attached to frame 32.

As noted earlier, containers 40A-G may be industry standard containers or customer containers also constructed of light yet strong material (e.g., plastic, wood, fiberglass, or aluminum). Containers 40A-G and/or carrier 30 may configured to be weather proof (e.g., water tight), to prevent damage to the items being shipped. Containers 40A-G are preferably constructed of material that is resilient enough so that each container may be shipped many times. Advantageously, this may reduce package costs and waste in the shipping process.

Figure 1K:
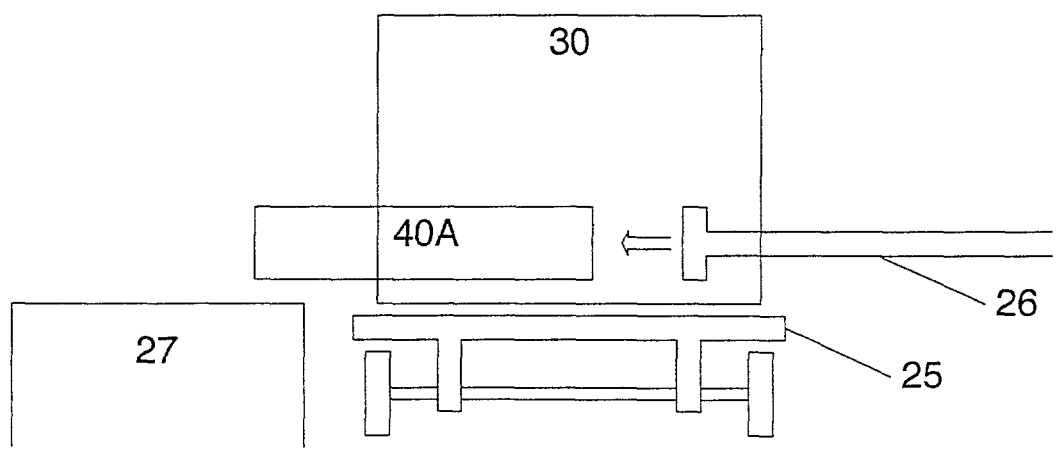
FIG. 1K illustrates one method for loading and unloading one embodiment of the container and carrier system from FIG. 1A.

Turning now to FIG. 1K, one embodiment of carrier 30 that allows automated packing and unpacking of containers is shown. In this embodiment, two opposing sides of container 30 are opened to allow an automated pusher arm 26 to push a selected container (i.e., container 40A in this example) onto a loading platform 27. As shown in the figure, the automated pusher arm 26 and loading dock 27 may be positioned so as to allow carrier 30 to be loaded and unloaded without being removed from the vehicle 25 that is transporting the carrier (e.g., the rail car or flat bed trailer).

FIGS. 2-3: Example of Efficient Shipping

Turning now to FIGS. 2 and 3, one example of system for efficient shipping is shown. This example illustrates five regional shipping company hubs (e.g., transfer points) located in San Francisco 80, Dallas 88, Chicago 82, Atlanta 86, and New York 84. Each hub is represented by a processing device (e.g., a computer configured to interface with memory devices 50A-N and/or 60). FIG. 3 illustrates that a typical shipping charge might be $80.00 for placing a container of goods on a direct flight from San Francisco to New York (or by using a single shipping company), while an indirect routing from San Francisco through Dallas and Atlanta to New York may yield a final cost of only $45.00. (i.e., $20.00 from San Francisco to Dallas, $10.00 from Dallas to Atlanta, and $15.00 from Atlanta to New York). Depending on the schedules involved, the container may take longer to arrive at its final destination, but in many instances customers may be willing to accept longer shipping times in exchange for a lower shipping cost. In this example, each shipping company may have one or more carriers (e.g., similar to carrier 30) that are shipped on a periodic basis to and from each hub city. For example, the shipping company 80 in San Francisco may have one carrier that is shipped daily to Chicago and one container that is shipped daily to Dallas. Regional shipping companies 82 and 88, in Chicago and Dallas respectively, may ship the carriers back also on a periodic basis (e.g., the next day). Similarly, shipping companies 82 and 88 may have carriers that are shipped on a periodic basis to Atlanta and New York. Advantageously, by using standardized containers (e.g., containers 40A-N) and/or standardized carriers (e.g. carrier 30), the transfer of goods at the regional shipping companies may be simplified. Similarly, the use of memory devices 60 and 50A through 50N may further increase the efficiency of the transfer of goods in the shipping hubs.

In one embodiment, each regional shipping company or hub 80-88 may be configured with a container processing apparatus that is directly or indirectly connected to a network 92. In one embodiment, as shown in the figure, network 92 is used to couple the processing apparatuses to a central server 90. While different types of networks may be used, in one embodiment the processing devices at the regional shipping company hubs and central server 90 may be connected via the Internet. In some implementations, the central server 90 may be configured to routinely poll each regional hub to determine availability, shipping times, and prices. Central server 90 may be configured to maintain a database of this information that is periodically updated. A customer wishing to ship an item may then contact one of the regional shipping companies or the central server directly (e.g., via the Internet). The customer may be prompted to provide information about the package to be shipped (e.g., size, weight, origination, final destination, shipping deadline, and any insurance or special handling requirements). If this information is provided to a regional shipping company or hub, the company or hub may then forward the information to central server 90 of an intelligent shipping agent to query the database for a quote. In response, central server 90 may execute an optimization program configured to search out the most efficient (e.g., lowest cost) routing for the package within the specified time constraints. Central server 90 included in the intelligent shipping agent may also have information about traditional shipping alternatives (e.g., direct routing using one shipping company) for comparison.

In one embodiment, the central server 90 may maintain real time price and shipping quotes by periodically monitoring shipping companies and hubs. For example, the central server 90 may have a constant high-speed Internet connection that allows communication with other pricing computers or services. By maintaining real time price and shipping quotes, intelligent shipping agent may route the container through the most cost-efficient route possible.

In another embodiment, the central server 90 and the intelligent shipping agent may be configured to calculate real-time conversions of the currency of the customer's choice. For example, for an American purchaser buying from a Japanese vendor, the customer may opt to have the currency converted from Japanese Yen to U.S. Dollars in real time at the time of the shipment. This conversion may be performed by querying a financial institution's server for a conversion rate (e.g., in parallel with performing the search based on efficiency). This embodiment may be particularly advantageous for currencies that have high fluctuations during any given day. The conversion rate may also be applied to other parts of the final cost, including for example, insurance and freight costs.

FIG. 4: Data File

Turning now to FIG. 4, one embodiment of a data file stored in memory device 50A is shown. In this embodiment, the data file includes the following: a unique item identification number (e.g., a package tracking number) 51, a description of the goods being shipped 60, the weight of the goods being shipped 61, any special shipping instructions (e.g., temperature, humidity, and vibration restrictions) 52, insurance terms (e.g., the insurance carrier, the policy number, the amount of insurance, and any deductible amounts) 55, the original shipping date 62, the arrival deadline 63, the origination location 53, the destination 54, any payment terms 64, information about the sender (e.g., sender's name 65, sender's email address 66, sender's telephone number 67, sender's street address 68, sender's shipping company account number 69), information about the recipient (e.g., recipient's name 70, recipient's email address 71, recipient's telephone number 72, recipient's street address 73, recipient's shipping company account number 74), and information about one or more intermediate destinations (75 through 77). Item handling and item content information may include any of the data fields 51-77 described above. Item handling information generally includes data fields, which describe attributes associated with the sender, receiver, shipping company, and insurance company. Item content information generally includes data fields, which describe attributes associated with the item such as an identification number and a description of the item.

Depending upon the implementation, additional information may also be stored in memory device 50A (for example, fax numbers for the sender and/or recipient). Similarly, less information than is shown in the figure may also be stored in memory device 50A in some embodiments. Advantageously, in some embodiments memory device 50A may be used to simplify payment (e.g., for shipping, for any tariffs or customs charges, or for the goods themselves in a COD arrangement). For example, memory device 50A may include account numbers for the sender 69, and recipient 74. Other possibilities include credit card, debit card, and bank account information (e.g., so that upon successful shipment of the item, a customer can be billed for insurance and/or shipping). In some embodiments, the data stored in the memory device may be encrypted. The device used to read the data from the memory device (e.g., processing apparatus 198 from FIG. 9 or package processors 322-324 from FIG. 10, as described below) may have a public key or private key usable to decrypt the data in the memory device. In one embodiment, authorized users of the system may be given a public key stored on a smart card, magnetic swipe card, or other electronic data storage card (e.g., Sony Corporation's Memory Stick™). The data from the memory device may also copied and then sent in email (e.g., in encrypted form) via the Internet to one or more of the parties associated with the shipping transaction (e.g., the originator, the shipping company, the insurance company and the recipient).

Figure 5A:
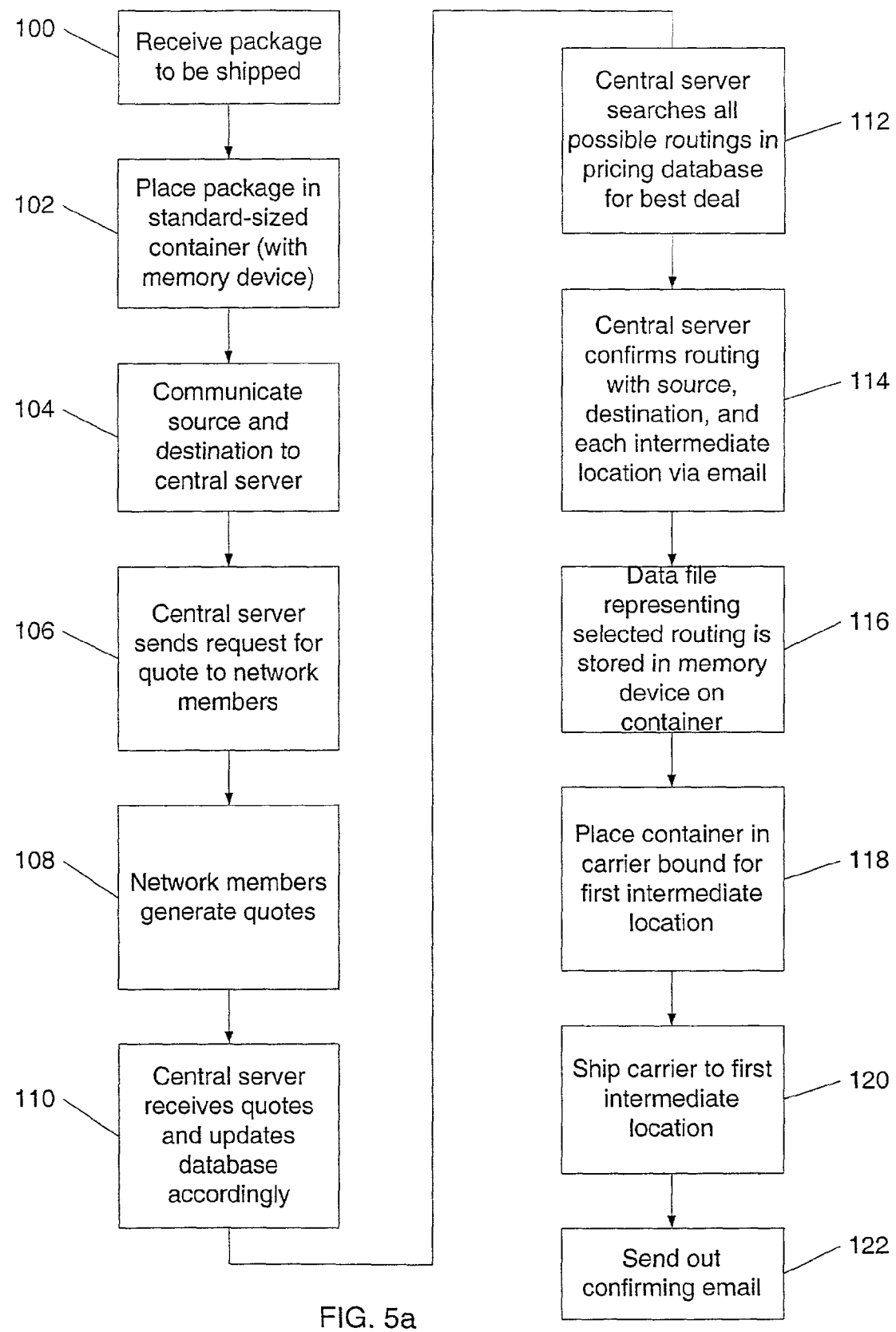
FIGS. 5a-b are flow charts illustrating one embodiment of a method for arranging shipment and insurance for an item.
Figure 5B:
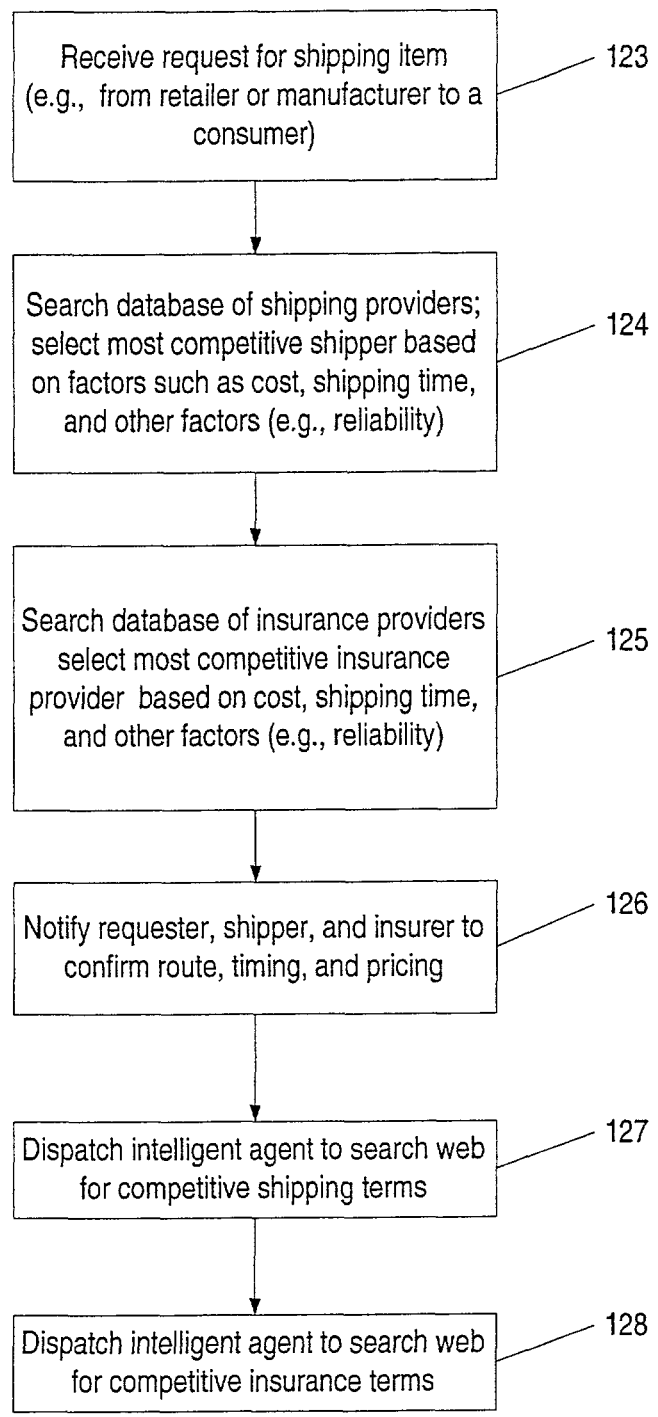

FIGS. 5a and 5b: Method for Arranging Shipping and Insurance for an Item to be Shipped Turning now to FIGS. 5a and 5b, one embodiment of a method to arrange for shipment and insurance, respectively, for a particular item being shipped or mailed is shown. A client of the intelligent shipping agent may contact the intelligent shipping agent to arrange the shipment (FIG. 5a) and insurance (FIG. 5b) for a particular item (Step 100). In one embodiment, the shipping company and the insurance company may be the same company if the shipping company also provides insurance coverage for the particular item. In one embodiment, the shipping company may partner with another insurance company to provide insurance coverage. In one embodiment, the shipping company may operate independently of each other. The shipping company may only offer shipment services and the insurance company may only provide insurance coverage for shipped items.

Referring to FIG. 5a, in one embodiment, the particular item may be placed inside a standard sized shipping container with an attached memory device (such as containers 40A-N with attached memory devices 50A-N) (Step 102). In one embodiment, the placing of the particular item inside the shipping container with an attached memory device may be performed by a shipping company, by the client or by the manufacturer of the particular item. Note, in some cases the container may not be used (e.g., if the item is already adequately packaged in a box that has the same dimensions as containers 40A-N). In these cases, the memory devices may be affixed directly to the particular item itself.

Next, information about the package to be shipped is transmitted to central server 90 of the intelligent shipping agent (Step 104). This information may include the origination and destination of the package, information about the type of package being shipped (e.g., the weight, any special shipping requirements such as temperature, humidity, or hazardous materials) and shipping dates (e.g., shipping deadlines). For example, insurance prices may be higher for goods that are perishable or require a minimum temperature during shipping. In some embodiments, the information may also include information (e.g., a list of carrier names, certifications, and/or qualifications) identifying qualified, approved, and/or exclusive carriers with which the package should be shipped (e.g., when increased security is desired). Central server 90 may then be configured to send out a request for quote based on this information to network members (Step 106) and other shipping companies. In another embodiment, the intelligent shipping agent may be configured to search a database for a quote for shipping cost. In another embodiment, central server 90 may be configured to periodically update the database independent of any request for quotes (e.g., by interrogating sources of external information for updated shipping and/or insurance information). In one embodiment, a first database may be maintained for shipping information and a second database may be maintained for insurance information. Two separate database searches may be conducted (e.g., serially or in parallel) by the intelligent shipping agent (e.g., in real-time) for locating shipping and insurance information. Alternatively, in a distributed environment without a central server 90, the intelligent shipping agent may distribute request for quotes directly to network members without central server 90. In response to the request for quote, network members may generate quotes for shipping costs for shipping the package to and from their shipping hub. (Step 108). For example, the shipping company in Dallas (see hub 88 in FIG. 2) may be configured to provide quotes for shipping the package from Dallas to New York and to Atlanta. Similarly, the shipping company in Chicago (see hub 82 in FIG. 3) may be configured to generate quotes for shipping the designated goods from Chicago to Atlanta and New York. The hub may also be referred to as an intermediary point.

In one embodiment, the client of the intelligent shipping agent may specify that the particular item needs to be picked up from a supplier S at location O and is to be delivered to a customer C at location D. In one embodiment, in response to receiving this information, the intelligent shipping agent may automatically send out a request for quotation to pick up the particular item at location O and deliver the particular item at location D. In another embodiment, the intelligent shipping agent may send out a first request for quotation to pick up the particular item at location O and deliver the particular item to an intermediary location I and a second separate request for quotation to pick up the particular item at intermediary location I and deliver the particular item to a final location D. In one embodiment, the shipping company may quote shipping costs for picking up the item from location O and delivering it to location D as a single amount based on the results from the corresponding first and second requests for quotation.

As noted above, in some cases more than one container may be needed to ship the package. In these cases, the network members may provide quotes for shipping only a subset of the packages if they do not have enough capacity to handle the entire set of containers or if a price differential is apparent for partial shipment. The central server may be configured to receive all of the quotes and update a database of shipping prices accordingly (Step 110). After the time period for responding to the request for quote has expired, the central server may be configured to search the response from the network members and/or all possible routings in the pricing database to determine the best deal for the customer (Step 112). Depending on the customer's requirements, some routings may be eliminated based on time (e.g., some routings may take too long and thus fail to meet the customer's shipping deadline). Some carriers may be excluded from consideration (e.g., if the customer and/or the customer's insurance company requires an approved or qualified carrier for security reasons).

The selection of the successful bidder may depend on various criteria such as cost efficiency, reliability, time to deliver, past history and geographic coverage. In one embodiment, the selection criteria may be based on securing the maximum value of a product or service at the least cost. Once the central server has selected a particular routing for the goods to be shipped, it may confirm this routing with the customer, the originating shipping company, the destination, and any intermediate locations/shipping companies (Step 114). In one embodiment, the confirmation may be in the form of a purchase order to deliver the particular item by picking the particular item from a supplier S at location O and delivering the particular item to a customer C at location D. This confirmation may be performed via the network (e.g., e-mail or instant messaging). The central server may also be configured to generate a data file that includes information about the goods to be shipped and the selected routing. As noted above, one embodiment of such a data file is shown in FIG. 4. This data file may be transmitted with the confirmation sent out by the central server in Step 114. The originating shipping company may update (if desired) and store a copy of the data file in the memory device that is attached to the container that will be used to ship the goods (Step 116). Next, the originating shipping company may place the container in a carrier 30 that is bound for either the final destination or an intermediate location as specified in the selected routing (Step 118). Selected information about the container may also be stored in the carrier's memory device, if desired. Next, the carrier is shipped to the first intermediate location (Step 120). As part of the shipping process, confirmation e-mail may be sent out to the central server and one or more of the parties associated with the shipment (e.g., the shipper, any intermediate shipping companies, and the recipient). (Step 122).

Advantageously, central server 90 may be configured to maintain a real time or near real time database of the status of all goods being shipped using the network. For example, a customer or shipping company may enter in a unique identifier that identifies the goods being shipped, and the database may respond by outputting the data file (e.g., as shown in FIG. 4). At any point before, during or after the shipping process the data file may be updated to match current conditions. For example, events such as arrival of the item at an intermediary destination, arrival at the final destination, damage to the item during shipment, and confirmation by the recipient of receiving the item may be conveyed to the central server, which may then update the database accordingly. Similarly, the updated information may be sent to any parties associated with the shipment (e.g., via e-mail). The intelligent shipping agent may be configured to interrogate external sources of information for shipping and insurance data on a periodic basis. The external sources of data may include third party databases or Internet web sites. The databases for shipping information and insurance information may be automatically updated by the intelligent shipping agent in real-time.

FIG. 5a may also be used to illustrate one embodiment of a method to arrange insurance for a particular item being shipped or mailed. A client of the intelligent shipping agent may contact the intelligent shipping agent to arrange the insurance for a particular item (Step 100). In one embodiment, the particular item may be placed inside a standard sized shipping container with an attached memory device (such as containers 40A-N with attached memory devices 50A-N) (Step 102). In one embodiment, the placing of the particular item inside the shipping container with an attached memory device may be performed by a shipping company, by the client or by the manufacturer of the particular item. Note, in some cases the container may need not be used (e.g., if the item is already adequately packaged in a box that has the same dimensions as containers 40A-N). In these cases, the memory devices may be affixed directly to the particular item itself.

Next, information about the package to be shipped is transmitted to central server 90 of the intelligent shipping agent (Step 104). This information may include the origination and destination of the package, information about the type of package being shipped (e.g., the weight, any special shipping requirements such as temperature, humidity, or hazardous materials), information related to the insurance of the shipped item (e.g., declared value of the insurance, deductible, description of the item insured and type of insurance coverage such as breakage, theft, and loss.), and shipping dates (e.g., shipping deadlines). Central server 90 may then be configured to send out a request for quote based on this information to network members (Step 106) and other insurance companies. In another embodiment, the intelligent shipping agent may be configured to search a database for a quote for shipping cost. In another embodiment, central server 90 may be configured to periodically update the database independent of any request for quotes. In one embodiment, a first database may be maintained for shipping information and a second database may be maintained for insurance information. Two separate database searches may be conducted by the intelligent shipping agent, in real-time, for locating shipping and insurance information. Alternatively, in a distributed environment without a central server 90, the intelligent shipping agent may distribute requests for quotes directly to network members without central server 90. In response to the request for quote, network members may generate quotes for insurance costs for shipping the package to and from their shipping hub. (Step 108). For example, the insurance company in Dallas (see hub 88 in FIG. 2) may be configured to provide quotes for insuring the package from Dallas to New York and to Atlanta. Similarly, the insurance company in Chicago (see hub 82 in FIG. 3) may be configured to generate quotes for insuring the designated goods from Chicago to Atlanta and New York. The hub may also be referred to as an intermediary point.

In one embodiment, the client of the intelligent shipping agent may specify that the particular item needs to be picked up from a supplier S at location O and is to be delivered to a customer C at location D. In one embodiment, the intelligent shipping agent may send out a request for quotation to provide insurance coverage from location O until delivery at location D. In another embodiment, the intelligent shipping agent may send out a request for quotation to provide insurance coverage from location O to an intermediary location I, and a separate request for quotation for insurance from the intermediary location I until delivery to a final location D. In one embodiment, the insurance company may quote insurance costs starting with picking up the item from location O and delivering it to location D.

As noted above, in some cases more than one container may be needed to ship the package. In these cases, the network members may provide quotes for insuring only a subset of the packages if they do not have enough capacity to handle the entire set of containers or if a price differential is apparent for partial shipment. The central server may be configured to receive all of the quotes and update a database of insurance prices accordingly (Step HOUND. After the time period for responding to the request for quote has expired, the central server may be configured to search the response from the network members and/or all possible routings in the pricing database to determine the best deal for the customer (Step 112). Depending on the customer's requirements, some routings may be eliminated based on time (e.g., some routings may take too long and thus fail to meet the customer's shipping deadline).

The selection of the successful bidder may depend on various criteria such as cost efficiency, reliability, time to deliver, past history and geographic coverage. In one embodiment, the selection criteria may be based on securing the maximum value of a product or service at the least cost. Once the central server has selected a particular routing for the goods or items to be shipped, it may confirm this routing with the customer, the originating shipping company, the destination, the insurance company, and any intermediate locations/shipping companies (Step 114). In one embodiment, the confirmation may be in the form of a purchase order to the insurance company to provide insurance for the particular item starting with the pick up of the particular item from a supplier S at location O and ending with the delivery of the particular item to a customer C at location D. The confirmation may be performed via the network (e.g., e-mail or instant messaging). The central server may also be configured to generate a data file that includes information about the items to be insured, shipped and the selected routing. As noted above, one embodiment of such a data file is shown in FIG. 4. This data file may be transmitted with the confirmation sent out by the central server in Step 114. The insurance company and/or the shipping company may update (if desired) and store a copy of the data file in the memory device that is attached to the container that will be used to ship the goods (Step 116). Next, the originating shipping company may place the container in a carrier 30 that is bound for either the final destination or an intermediate location as specified in the selected routing (Step 118). Selected information about the container may also be stored in the carrier's memory device, if desired. Next, the carrier is shipped to the first intermediate location (Step 120). As part of the shipping process, confirmation e-mail may be sent out to the central server and one or more of the parties associated with the shipment (e.g., the shipper, any intermediate shipping companies, the insurance company and the recipient). (Step 122).

Advantageously, central server 90 may be configured to maintain a real time or near real time database of the status of all goods being shipped using the network. For example, a customer or shipping company may enter in a unique identifier that identifies the goods being shipped, and the database may respond by outputting the data file (e.g., as shown in FIG. 4). At any point before, during or after the shipping process the data file may be updated to match current conditions. For example, events such as arrival of the item at an intermediary destination, arrival at the final destination, damage to the item during shipment, and confirmation by the recipient of receiving the item may be conveyed to the central server, which may then update the database accordingly. Similarly, the updated information may be sent to any parties associated with the shipment (e.g., via e-mail). The intelligent shipping agent may be configured to interrogate external sources of information for shipping and insurance data on a periodic basis. The external sources of data may include third party databases or Internet web sites. The databases for shipping information and insurance information may be automatically updated by the intelligent shipping agent in real-time.

Turning now to FIG. 5b, another embodiment of a method for arranging shipment and insurance for an item is shown. In this embodiment, a request for shipping services (or a request for a quote for shipping services) is received (step 123). The request is preferably received electronically (e.g., via a portal offering shipping and related logistics services). The request may including information such as the weight and/or size of the item, the starting point and destination for the item, the value of the item (i.e., insurance amount) and any deadlines for the item to arrive at the destination.

Next, two databases are searched in order to select the most cost effective shipping provider and insurance providers for the item (steps 124 and 125). The databases may be searched in parallel, or they may be searched in series. The first database may include shipping information that has been accumulated in order to allow rapid selection of the most cost effective shipping provider meeting certain minimum criteria (e.g., being able to provider delivery to the final destination with the predetermined deadline). Similarly, the second database may include a variety of insurance information including cost for different amounts of coverage, exclusions for certain types of items, and rating information on the financial stability of the insurer.

Next, the requester may be notified of the selected shipping provider and insurance provider and the cost (step 126).

The database searching and notification are preferably performed in real-time (i.e., without a significant delay perceived by the requester). The selected insurance provider and shipping provider may also be notified to confirm that shipment of the item is needed and to provide any detailed information needed to initiate the shipment (e.g., the address of the pick-up location and payment information).

In one embodiment, the databases are maintained by periodically dispatching intelligent agents that are configured to traverse a network such as the Internet to find web sites or other network-accessible databases (steps 127 and 128). The intelligent agents may be configured to query web sites belonging to third parties (e.g., shipping companies and insurance companies, agents or brokers) in order to update the databases with current information on pricing and other information relating to shipping and insurance. Advantageously, by periodically dispatching intelligent agents (or by periodically querying third party sites), one or more internal databases may be assembly, thereby allowing real-time queries to be performed. As described above, shipment using multiple carriers may be supported in this method. In other embodiments, reverse auctions may be initiated in order to populate the databases with current pricing information.

Figure 6:
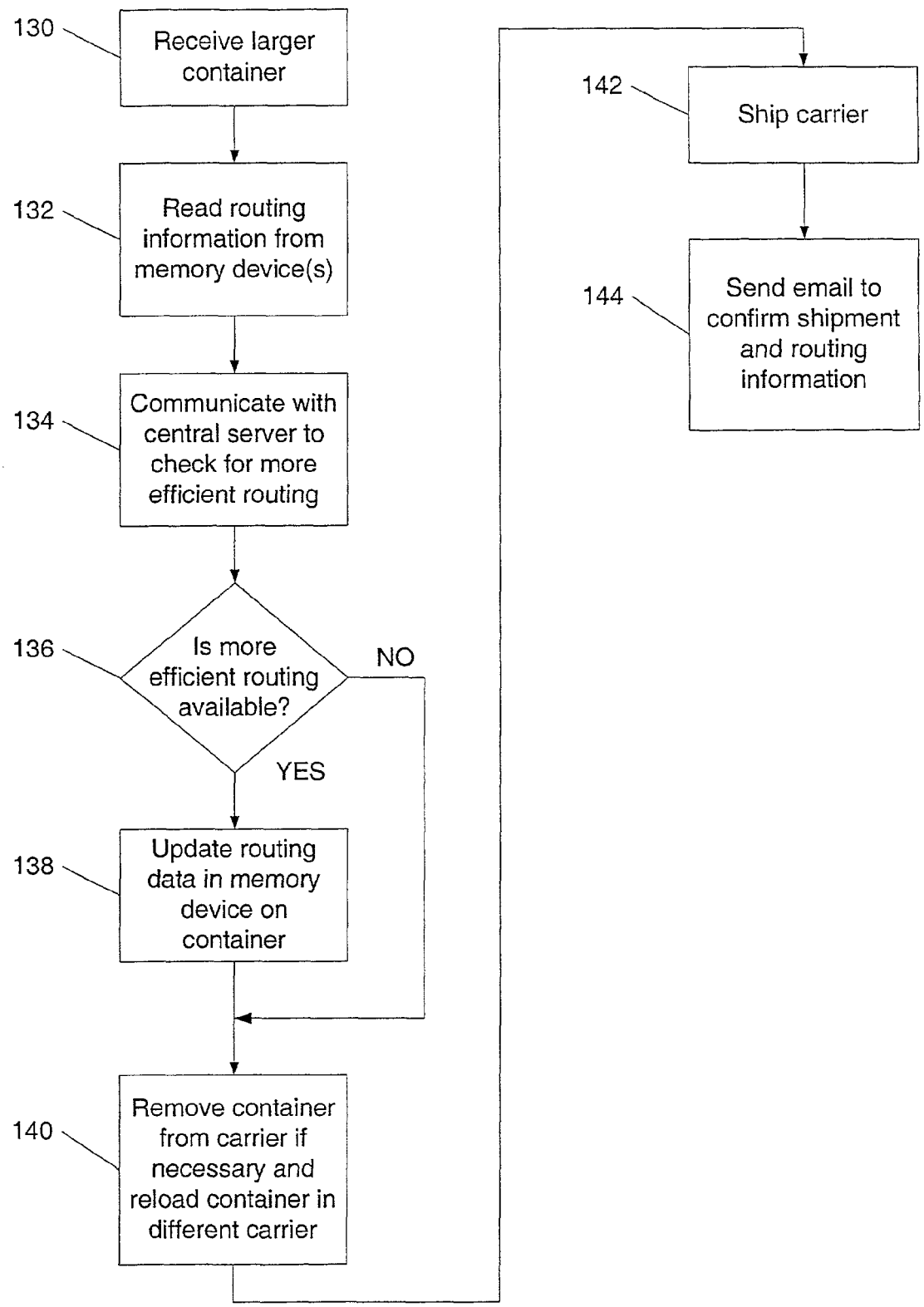
FIG. 6 is a flow chart illustrating another embodiment of a method for efficiently shipping packages.
Figure 7:
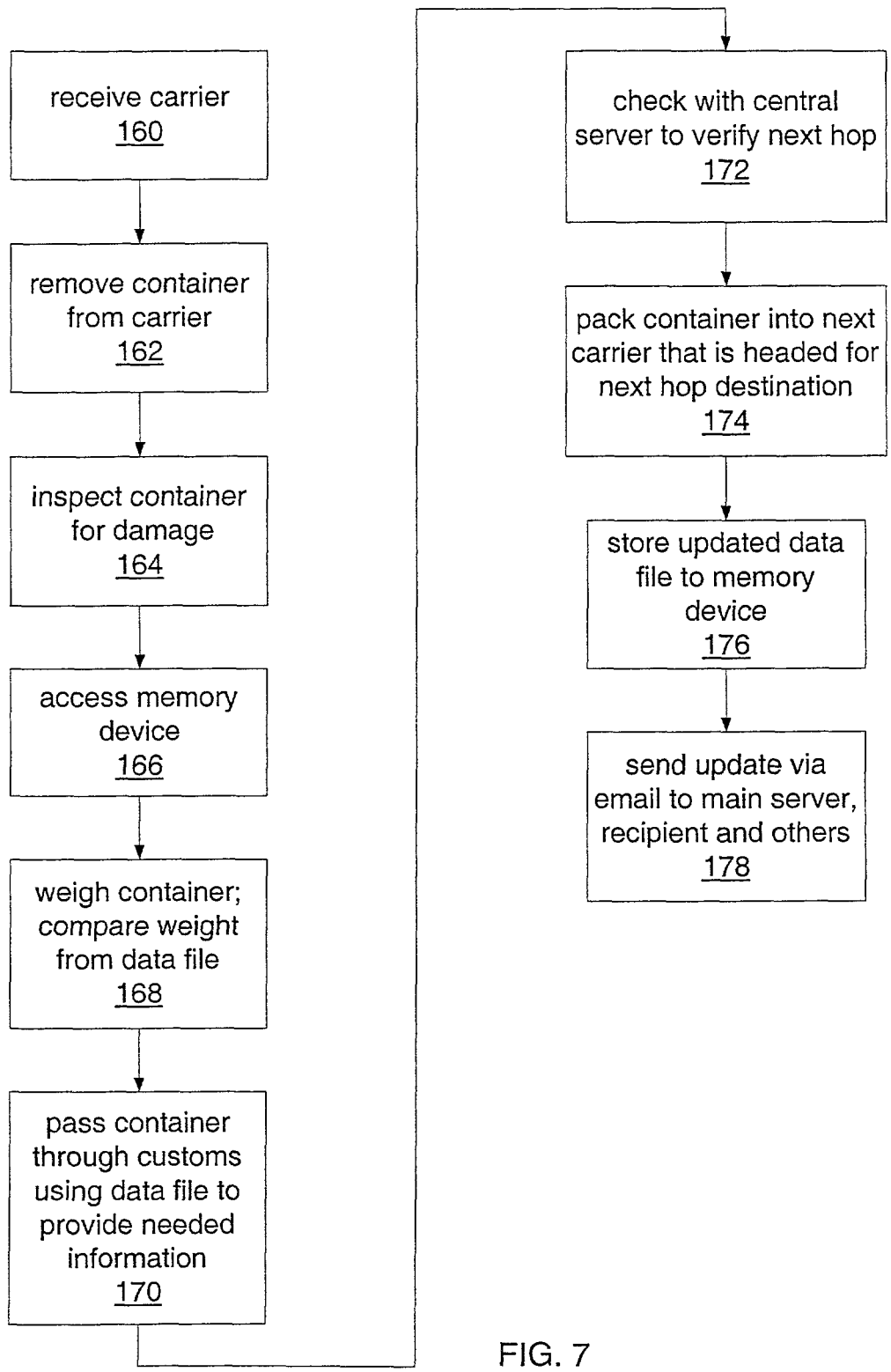
FIG. 7 is a flow chart illustrating yet another embodiment of a method for efficiently shipping packages.

FIGS. 6-7: Handling Packages at Intermediate Destination

Turning now to FIG. 6, a flowchart depicting one portion of one embodiment of a method for arranging shipment and insurance for an item being shipped or mailed is shown. In this figure, details of how the container may be handled upon arriving at an intermediate destination is shown. First, the container is received at the intermediate destination (Step 130). Next, the data file, or at least the routing information, may be read from the memory device attached to the container and/or the carrier (Step 132). Next, the shipping company may be configured to communicate or verify the receipt of the goods using the network. The shipping company may also communicate with the central server to check if more efficient routings from the intermediate destination to the final destination have become available (Step 134). For example, a particular shipment of goods may originally be routed from San Francisco to New York via Dallas and Atlanta. However, by the time that the shipment arrives in Dallas, a more direct routing from Dallas to New York may have become less expensive than a routing through Atlanta. This may be due to changes in shipping rates (e.g., airline shipping rates), price wars, the cancellation of other shipments leading to excess capacity, or other factors. Thus, central server 90 may be configured to determine whether or not there is a more efficient routing available. (Step 136). If there is a more efficient routing available, server 90 may be configured to convey this information to the shipping company in Dallas, which may then update the routing information in the memory device 50A affixed to the shipping container (Step 138). Similarly, server 90 may be configured to update the information on the server's database for access by any party to the shipping transaction (e.g., the originator, the final recipient, and any shipping companies involved in the transaction). Once the routing for the remainder of the shipment has been determined, the regional shipping company (e.g., the shipping company that has received the container in Dallas), may remove the container from the carrier and reload the container into a different carrier that is destined for the next intermediate destination or the final destination (Step 140). As part of this process, the shipping company may also update the memory device on the carrier to reflect the newly added container. Next, the carrier is shipped (Step 142), and a confirmation may be transmitted to central server 90 and/or one or more of the parties to the transaction (Step 144). In one embodiment, the confirmation may be sent as an e-mail, instant message via the Internet, or a text-to-speech message via telephone. As noted above, the confirmation may include a copy of the updated data file.

Turning now to FIG. 7, another embodiment of a method for handling the containers at an intermediate or final destination is shown. This embodiment assumes that additional processing is performed on the shipped goods to ensure that the goods have arrived in acceptable condition. First, the carrier is received (Step 160). Next, the container may be removed from the carrier (Step 162). The container may be visually inspected for damage (Step 164). For example, in one embodiment digital cameras may be used to take pictures of the container and/or goods within the container to verify their condition. In some implementations, these digital image files may be appended to the data file and transmitted to central server 90. An infrared scanner may be used to check for suspicious or threatening container contents. In another embodiment, automated scanning devices may be used to inspect the container for damage. For example, each container may have a pattern imprinted on its sides. Any damage to the container (e.g., dents, or gouges) may be detected as by a digital camera that scans for the imprinted pattern. For example, a regularly spaced grid or series of lines may be imprinted on the surface of the carrier (e.g., a black and white bar code). Damage to the device will most likely result in variations to the pattern, and the processing unit may be configured to detect these variations and signal a problem to the operator or the central server. In one embodiment, the insurance company may be automatically alerted on detecting damage to the container.

In some embodiments, the container may be inspected by an air testing or sampling device (or the memory device may contain such a device) in order to check for contaminants that the container may have been exposed to. For example, in one embodiment, the air testing or sampling device may check for biological contaminants (e.g., by performing DNA analysis) such as anthrax spores. In embodiments where the air testing or sampling device is included in the memory device, the air testing or sampling device may be configured to periodically test air samples and to store the results of the tests in the memory device. If a suspicious substance is detected, the container may be rerouted to an appropriate facility (e.g., customs, a designated testing laboratory, an FBI facility, etc.) for further testing and/or decontamination. The shipper and/or recipient may also be notified if a suspicious substance is detected. Alternatively (or additionally), the container may be treated (e.g., by a decontaminant such as ultraviolet light, radiation, bleach, etc.) in order to destroy any biological contaminants.

Similarly, if the container's memory device is outfitted with an environmental sensor, then the processing unit may be configured to read the contents of the memory device to ensure that the container has not experienced any environmental extremes or problems. For example, assuming that there are delicate glass components in the container, and if the environmental sensor detects that a vibration exceeding a predetermined maximum threshold has occurred, then the processing unit may signal an alert to the operator. The operator may then notify the insurance company, the shipper and recipient and possibly check the shipped items for damage. Advantageously, if the items have been damaged due to the vibration, the container may be returned to directly to the originating party from the intermediate destination without incurring the additional cost and wasted time of shipping the container all the way to the final destination before finding out that the items inside have been damaged.

Once the container has been inspected for damage, any damage or problems may be noted and appended into the data file. As noted above, the data file may be stored to the memory device and also conveyed to central server 90 (block 166). In addition to damage, the container's weight may be compared with the memory device's weight information stored in the data file. (Step 168). While the use of weight may be optional, it may be particularly advantageous in international shipping where concerns such as smuggling often arise. By insuring that the weight of the package as received is the same as the weight of the package as shipped, customs officials may be less concerned with additional items being smuggled in the container and thus less likely to open the container and thereby delaying shipment. (Step 168). Additional information to assist in the customs process may also be read from the data file (Step 170). For example, a declaration of the type of goods in the container may be read from the memory device.

As previously noted, the central server may be contacted to verify the next intermediate destination (e.g., to check for cheaper routings). (Step 172). Next, the container is packed into a different carrier (if necessary) that is headed to the next intermediate destination or the final destination (Step 174). As noted above, in the event that multiple containers have been shipped together, the containers may take different routings to the final destination. The updated data file may be stored to the memory device on the container and/or carrier (Step 176). Similarly, the updated data file and/or a confirmation of shipment may be conveyed to central server 90 and any party to the shipping transaction (Step 178).

In one embodiment, the container may be shipped by airline and rerouted at different airports at intermediate destinations or hubs. In another embodiment, the container may be shipped using trains, ground transport shipping trucks, local bus services, and taxi cabs. For example, a container may be routed by central server 90 through current ground transportation, such as buses, taxis and trains. This embodiment may be used for local transport, while airlines may be used for long distance transport of the container. In one embodiment, central server 90 may interface with a traffic control system that coordinates each ground transport, such as taxis, trains and buses, to receive requests in real time and to convey any requests for transport to each ground transport system. In one embodiment, taxi companies and bus services may interface with central server 90 periodically to check for containers needing transport before making fare trips locally. In another embodiment, passenger and freight trains may interface with central server 90 to check for containers needing transport before making trips between stops or destinations. In one embodiment, at each intermediate destination central server 90 may check for cheaper routes using passenger or freight trains scheduled to arrive at another intermediate or the ultimate destination.

Figure 8:
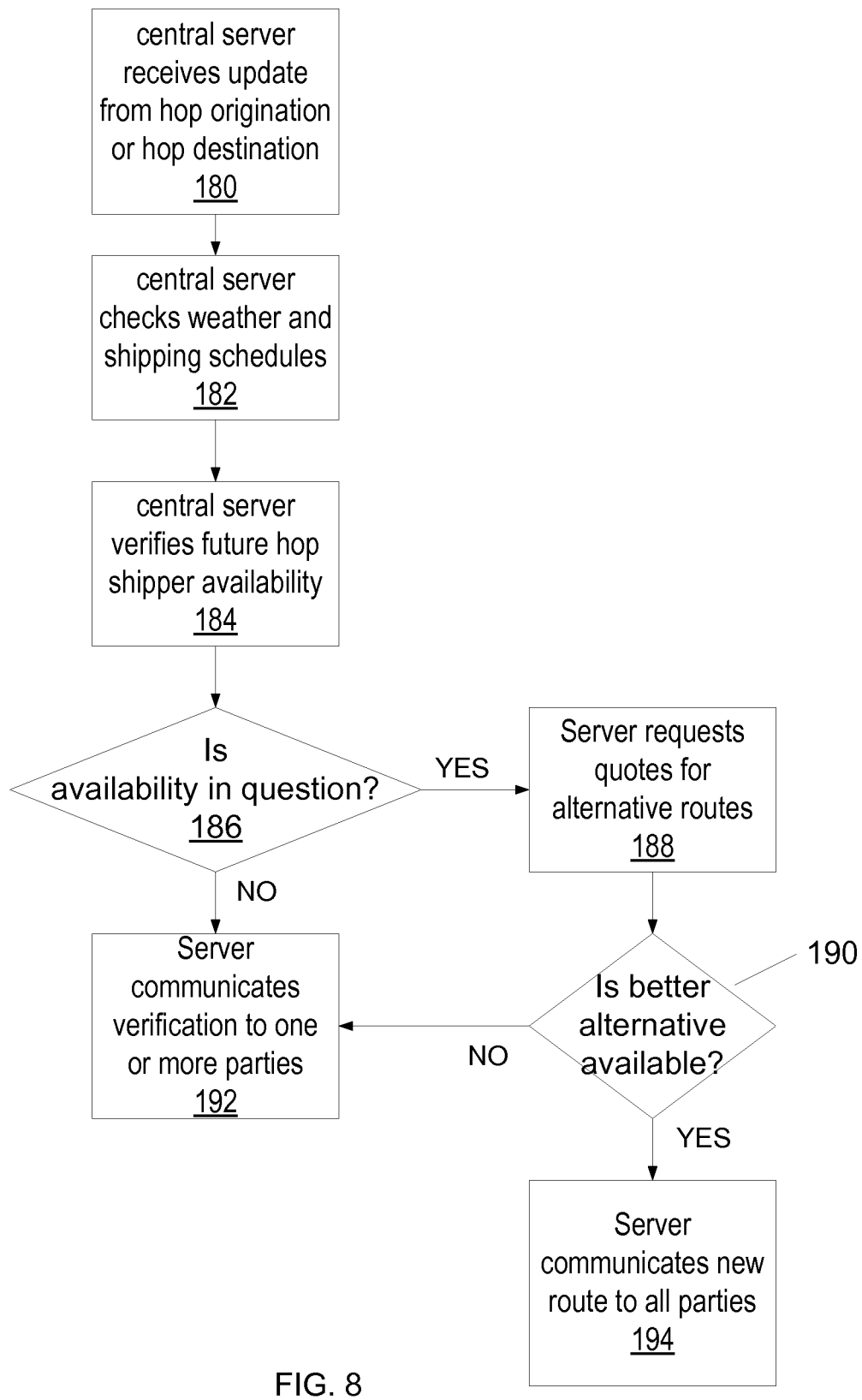
FIG. 8 is a flow chart illustrating another embodiment of a method for efficiently shipping packages.

FIG. 8: Operating Central Server

Turning now to FIG. 8, one embodiment of a method for operating central server 90 is illustrated. In this embodiment, central server 90 may be configured to receive updates at any time before, during or after the shipping process. This includes updates received from intermediate destinations I (Step 180). Central server 90 may be configured to periodically check shipping schedules for subsequent intermediate destinations (Step 182) to verify the availability and/or feasibility of the future intermediate destination (Step 184). If availability of shipment through one or more of the subsequent intermediate destinations I is in question (Step 186), then the server may be configured to request quotes for alternate routes (Step 188). If one or more better alternative routes are available (Step 190), then the server may then communicate the newly selected route to all parties to the shipping transaction (Step 194). For example, in one embodiment the central server may be configured to check weather forecasts and/or travel advisories for selected intermediate destinations. If Chicago is an intermediate destination for a particular shipment scheduled to arrive on the 22nd of January, and if Chicago is experiencing a serious blizzard with travel advisories on the 21st of January just prior to initiation of the shipment, the central server may be configured to attempt to re-route the shipment to avoid the weather problems in Chicago. Similarly, if the regional shipping company in Chicago has indicated that it has a two-day backlog of packages to ship out, the central server may use that information to find an alternate route. If, however, no issues concerning availability of shipment at intermediate destinations arise, or if no better alternatives are available, then the central server may simply be configured to communicate a verification of the original route to one or more of the parties to the shipping transaction (Step 192).

Figure 9:
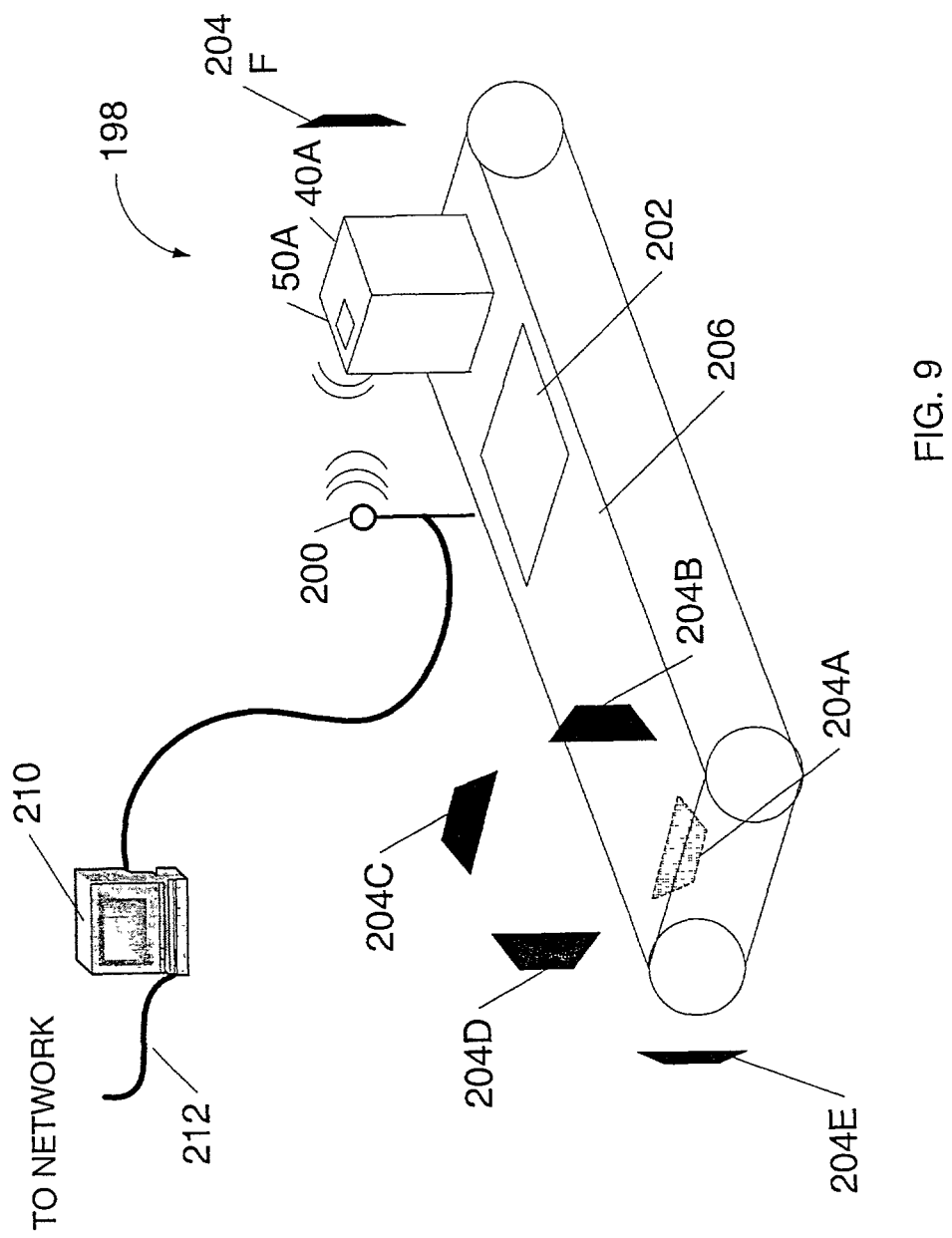
FIG. 9 illustrates one embodiment of an apparatus for processing packages.

FIG. 9: Apparatus for Package Processing

Turning now to FIG. 9, one embodiment of a package processing apparatus 198 for efficiently handling shipment of containers (e.g., container 40A) is shown. In this embodiment, the apparatus (also referred to herein as a package processing unit) comprises a conveyor belt 206. As shown in the figure, conveyor belt 206 is configured to convey container 40A over a weighing device 202. The apparatus may further comprise a communications device 200 configured to communicate with, and read the contents of, memory device 50A.

In some embodiments, the apparatus may further comprise one or more digital cameras (e.g., 204A through 204F). As previously noted, these digital cameras may be configured to capture images of the carrier, container, and/or the item itself. In some embodiments (assuming there is enough storage available in the memory device), these images may be stored in the memory device by the package processing unit using communications device 200 or they may be communicated to the central server via the network. Note, this figure merely illustrates one possible embodiment for the apparatus and other embodiments are possible and contemplated. For example, in one embodiment the apparatus may be implemented as a handheld device without conveyor belt 206. The handheld device may include communications device 200 to communicate with memory device 50A, and a digital camera configured to capture images of the container 40A. Other embodiments may be configured without digital cameras. Communications device 200 may, for example, be a wireless link, a physical cable that connects to memory device 50A, or a removable media reader (e.g., a CD-RW drive).

Advantageously, the package processing apparatus described above may be installed at locations such as ports, warehouses, airports, distribution centers, and shipping companies. The operation of the apparatus may advantageously be automated (e.g., with a mechanical arm to automatically remove and insert containers into carriers and/or to automatically read and write data to the memory device). The apparatus may further comprise an interface to a computer system 210. Computer system 210 may in turn be connected to a network (e.g., the Internet) by link 212. The computer system may communicate with the apparatus in order to convey the captured data (e.g., from memory device 50A and digital cameras 204A-F) to central server 90. As noted above, in other embodiments the apparatus may include an internal computer or microprocessor with a built-in wireless network connection and scanning device.

Advantageously, by accessing the intelligent shipping agent, e.g., the data files stored in central server 90's database (e.g., by using an Internet website), any party to the shipping transaction may be able to immediately determine where the package is and which shipping company is currently in charge of the package. As previously noted, additional information may also be available (e.g., any damage that the device may have sustained or any environmental extreme the container may have experienced).

Another potential advantage of some embodiments of the system and method described above is the ability of any party to the transaction to alter the final destination conveniently. For example, a package being shipped from Tokyo to New York may have the final street address altered by accessing the central server and entering the new final destination address. In a traditional system wherein the destination address is affixed to the package in an unchangeable manner, there is no convenient way to update the final delivery address. In contrast, using the method described above the updated address in central server's database may be downloaded to the memory device on the carrier or container at any intermediate destination. Confirmation of the final destination address change may be automatically sent to all relevant parties in the shipping transaction.

In some embodiments, the central server may be configured to automatically notify one or more parties to the shipping transaction upon the occurrence of predetermined events. For example, once the package reaches a particular intermediate destination or the final destination, the central server upon receiving confirmation of this may be configured to automatically contact the designated recipient (e.g., by an automated call to a telephone or cell phone number, or by e-mail, paging, or instant messaging). Similarly, local trucking companies or shipping companies may be notified automatically as soon as the package arrives at a particular intermediate or final destination.

In some embodiments, the unique identification number associated with a particular item may be assigned by central server 90 included in an intelligent shipping agent. In other embodiments, the local shipping company may assign this number after verifying that there is no other package currently using the number in central server 90's database. In some embodiments, the unique ID number may be shared with one or more shipping companies that handle the package from its origination to its final destination. For example, assuming a package is shipped by airlines A and then delivered by trucking company B, airline A and trucking company B may both be provided access central server 90 to read the data file. The unique identification number may be selected in a format such that it is useable both by airline A's and trucking company B's computers systems. In one embodiment, central server 90 may be configured to contact the servers of airline A and trucking company B in order to select a unique identifier that is also useable by those company's computer systems. Advantageously, this unique identifier may also be used to control billing receipts and customs records for the shipped item.

In one embodiment, the intelligent shipping agent may be implemented as a number of different servers such as central server 90 (e.g., one server in each country serviced by shipping companies that are part of the network). Advantageously, if the number of e-mails or instant messages generated by the network of shipping companies becomes too large, distributing the processing among multiple servers may advantageously reduce the e-mail traffic burden. The data file associated with a particular package may be stored only on the server residing in the originating country. In one embodiment, the data file may be formatted using XML, SGML, HTML, or another type of mark-up language or data file format. Advantageously, XML offers several potential advantages including the ability to format data such that it may be more easily imported into SQL databases.

Figure 10:
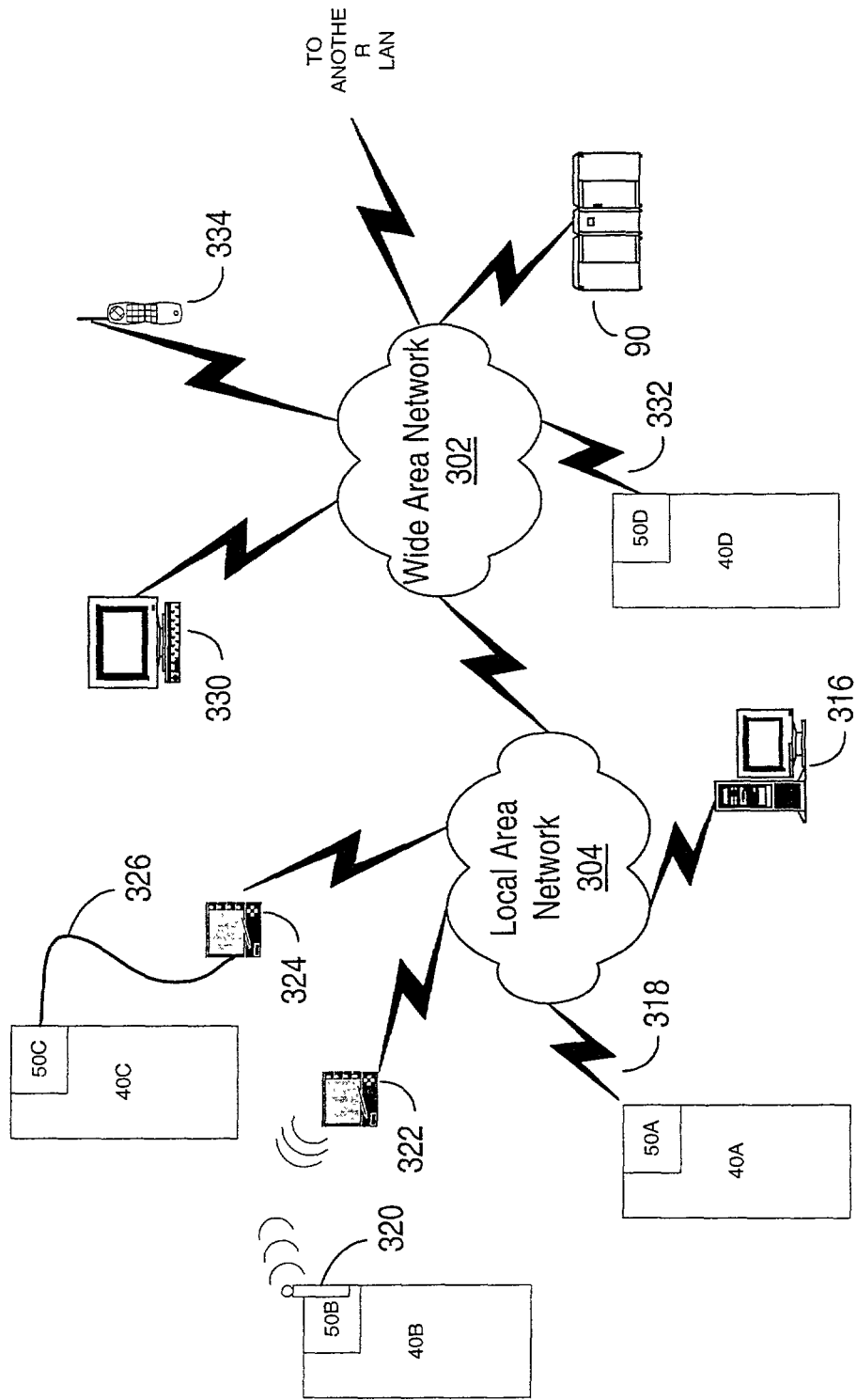
FIG. 10 illustrates one embodiment of a network usable to implement the systems and methods described herein.

FIG. 10: Wide Area Network

Turning now to FIG. 10, one embodiment of a wide area network (WAN) that may be used to implement the intelligent shipping agent system described above is shown. WAN 302 is a network that spans a relatively large geographical area. The Internet is an example of WAN 302. WAN 302 typically includes a plurality of computer systems which are interconnected through one or more networks. Although one particular configuration is shown in the figure, WAN 302 may include a variety of heterogeneous computer systems and networks which are interconnected in a variety of ways and which run a variety of software applications.

One or more local area networks (LANs) 304 may be coupled to WAN 302. A LAN 304 is a network that spans a relatively small area. Typically, a LAN 304 is confined to a single building or group of buildings (e.g., one airport or shipping hub). Each node (i.e., individual computer system or device) on a LAN 304 preferably has its own CPU with which it executes programs. LAN 304 allows many users to share devices (e.g., printers) as well as data stored on file servers. The LAN 304 may be characterized by any of a variety of types of topology (i.e., the geometric arrangement of devices on the network), of protocols (i.e., the rules and encoding specifications for sending data, and whether the network uses a peer-to-peer or client/server architecture), and of media (e.g., twisted-pair wire, coaxial cables, fiber optic cables, radio waves).

Each LAN 304 includes a plurality of interconnected computer systems and optionally one or more other devices: for example, one or more personal computers 316, and one or more package processing apparatuses 322-324. Package processors 322-324 may, for example, be hand-held devices (e.g., used in connection with a forklift, crane, or automated loading and unloading station as shown in FIG. 1K) or conveyor-belt devices as previously described. As illustrated in the figure, some package processors (e.g., processor 322) may be configured to communicate with container memory devices (e.g., container 40B) via a wireless link 320. Other package processors (e.g., processor 324) may communicate with the memory device 50C of a received container 40C by a physical link 326. As also noted above and illustrated at 318, in some embodiments, some configurations of container 40A may have a memory device 50A that is configured to communicate directly with LAN 304 and/or WAN 302 (see e.g., container 40D and memory device 50D). For example, LAN 304 may constructed at a shipping hub (e.g., an airport, dock or warehouse) and may be configured to use a wireless access protocol that supports the dynamic addition and remove of devices (e.g., using Sun Microsystems Inc.'s Jini® protocol). Whenever a container is brought within range of the wireless LAN, then the containers' memory devices (e.g., using internal processors and wireless links such as link 320) may access the network and communicate their data.

Central server 90 may coupled to multiple LANs via WAN 302. As described above, central server 90 may be configured to convey email verification messages to one or more computers (e.g., personal computers 316 and 330) connected to WAN 302 or LAN 304. Central server 90 may also be configured to send text of voice messages (e.g., pages) to cell phones (e.g., cell phone 334) or pages as specified by the parties to shipping transaction.

Figure 11:
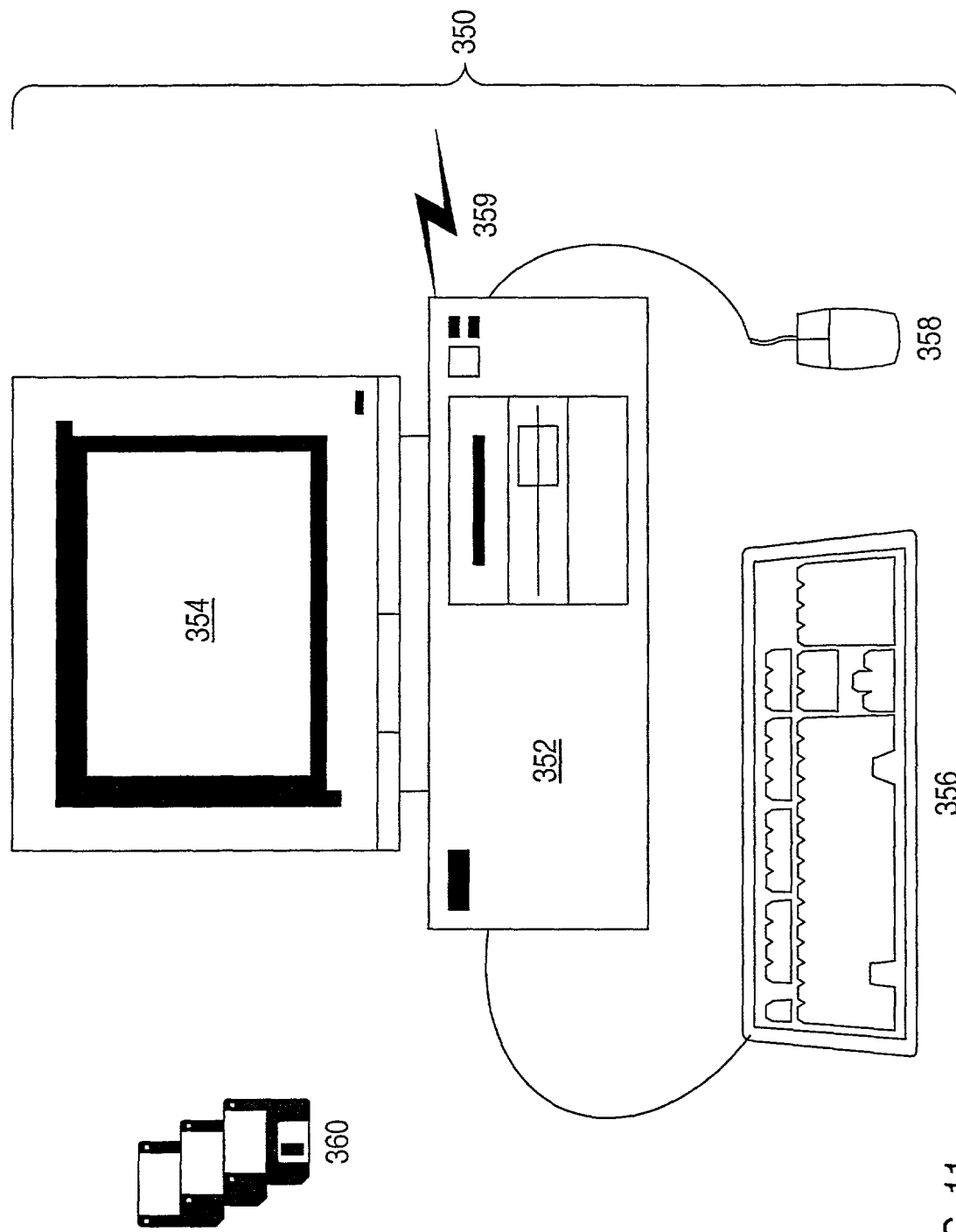
FIG. 11 illustrates one embodiment of a computer system usable to implement the systems and methods described herein.

FIG. 11: Typical Computer System

FIG. 11 illustrates a typical computer system 350, which is suitable for implementing various embodiments of the systems and methods described above. Each computer system 350 typically includes components such as a CPU 352 with an associated memory medium such as floppy disks 360, CD-ROMs, or DVDs (not shown). The memory medium may store program instructions for computer programs, wherein the program instructions are executable by the CPU 352. The computer system 350 may further include a display device such as a monitor 354, an alphanumeric input device such as a keyboard 356, communication device such as a modem 359 and a directional input device such as a mouse 358.

In one embodiment, the computer system 350 may be configured to execute a computer program to access containers' memory devices using one or more interfaces as described herein. In another embodiment, the computer system 350 may be a central server (e.g., such as central server 90) operable to execute a computer programs to create and manage the database of routing information as described herein. Other embodiments of the computer system 350 are also possible and contemplated.

The computer system 350 preferably includes a memory medium on which computer programs according to various embodiments may be stored. The term "memory medium" is intended to include an installation medium, e.g., a CD-ROM, or floppy disks 360, a computer system memory such as DRAM, SRAM, EDO RAM, Rambus RAM, or a non-volatile memory such as a magnetic media, e.g., a hard drive, or optical storage. The memory medium may include other types of memory as well, or combinations thereof. In addition, the memory medium may be located in a first computer in which the programs are executed, or may be located in a second different computer, which connects to the first computer over a network. In the latter instance, the second computer provides the program instructions to the first computer for execution. The computer system 350 may also include a time keeping device such as a real-time clock. The real-time clock of the computer system 350 may be, periodically or on demand, synchronized with a global standard time clock. Also, the computer system 350 may take various forms, including but not limited to a personal computer system, mainframe computer system, workstation, network appliance, Internet appliance, personal digital assistant (PDA), Internet enabled cellular telephones, or any other similar device. In general, the term "computer system" can be broadly defined to encompass any device having a processor, which executes instructions from a memory medium.

The computer system's memory medium preferably stores a software program or programs for performing the methods for efficient shipping as described herein. The software program(s) may be implemented in any of various ways, including procedure-based techniques, component-based techniques, and/or object-oriented techniques, among others. For example, the software program may be implemented using ActiveX controls, programming languages such as C++, Java, Visual Basic, object oriented software based on COM/DCOM and/or CORBA objects, JavaBeans, Microsoft Foundation Classes (MFC), browser-based applications (e.g., Java applets), traditional programs, or other technologies or methodologies, as desired.

Although the embodiments above have been described in considerable detail, other versions are possible. Numerous variations and modifications will become apparent to those skilled in the art once the above disclosure is fully appreciated. It is intended that the following claims be interpreted to embrace all such variations and modifications.

What is claimed is:

1. A method, comprising:
performing via a server:
receiving a request to ship an item and to insure the item during shipment from an origination to a final destination, wherein the request specifies the origination, the final destination, insurance information, and item information;
prior to shipment of the item as a packaged item, and in response to said receiving the request:
automatically performing a search to select particular insurance for the packaged item according to one or more insurance criteria, wherein said performing the search to select particular insurance is based on the insurance information in the request to provide a specified level of insurance coverage for the packaged item during said shipment;
automatically performing a search to select a designated routing for the packaged item, wherein the search to select the designated routing comprises:
determining an indirect route to be less costly than a more direct route, wherein the indirect route is longer than the more direct route,
verifying that the indirect route meets a delivery deadline for the packaged item arriving at the final destination, and
selecting, based on said determining an indirect route to be less costly than a more direct route and based on said determining that both the indirect route and the more direct route are sufficient to meet the delivery deadline, the indirect route as a designated routing for the packaged item from the origination to the final destination as specified in the request;
determining item information including one or more characteristics of the packaged item, the characteristics including one or more of a weight of the item, an image of the item, or a description of the item;
determining insurer information including one or more terms of said particular insurance, the insurer information specifying the insurer selected to provide said particular insurance during said shipment;
determining routing information specifying the designated routing for the packaged item, the routing information specifying segments of a multi-segment route from the origination to the final destination; and
storing the item information, the insurer information, and the routing information as contents of a memory device which accompanies the packaged item during said shipment, wherein the memory device comprises an interface to update the contents, via a remote device, before, during, and after said shipment;
updating the contents of the memory device via the interface of the memory device during the shipment of the packaged item and the memory device from the origination to the final destination, wherein the server remotely updates a data file stored on the memory device;
accessing the updated contents of the memory device during the shipment of the packaged item and the memory device from the origination to the final destination, wherein the server receives the updated data file from the memory device via the interface of the memory device subsequent to the server remotely updating the data file stored on the memory device; and
during the shipment of the packaged item and the memory device from the origination to the final destination, receiving, by the server, updated information from the memory device.

2. The method as recited in claim 1, further comprising:
in response to receiving the updated information from the memory device, determining a new routing from a current location of the packaged item to the final destination; and
updating the memory device with information for the new routing.

3. The method as recited in claim 1, wherein the packaged item becomes packaged by packing the item in a container for shipping, wherein the container is configured to fit with multiple other containers in a carrier.

4. The method as recited in claim 1, further comprising forwarding copies of at least a portion of the contents of the memory device to one or more parties involved in said shipment, wherein the one or more parties include at least an originator of the request to insure the item during said shipment, a recipient of the item at the final destination, and the insurer selected to provide said particular insurance.

5. The method as recited in claim 1, further comprising forwarding copies of the contents of the memory device to one or more predetermined email addresses.

6. The method as recited in claim 1, wherein the information is collected by a sensor of the memory device.

7. The method as recited in claim 1, wherein the designated routing is the least expensive routing.

8. The method as recited in claim 1, wherein the contents of the memory device include contact information for the insurer selected to provide said particular insurance.

9. The method as recited in claim 1, further comprising storing the contents of the memory device on a server connected to a network, wherein the server provides access to the contents of the memory device via the network.

10. The method as recited in claim 1, wherein said storing the information as contents of the memory device comprises storing the contents of the memory device in an XML format.

11. The method as recited in claim 1, wherein the updated data file comprises updated address information for a destination of the packaged item.

12. The method as recited in claim 1, wherein the item information in the contents of the memory device further comprises customs information for the item.

13. The method as recited in claim 1, wherein the item information in the contents of the memory device further comprises item handling information.

14. The method as recited in claim 13, wherein the item handling information comprises special instructions based on temperature, humidity, or vibration restrictions for shipping the item.

15. The method as recited in claim 1, wherein the insurer information in the contents of the memory device further comprises one or more of: an insurance policy number that identifies the particular insurance, an amount of insurance provided by the particular insurance, and an insurance deductible for the particular insurance.

16. The method as recited in claim 1, wherein the item information in the contents of the memory device further comprises one or more digital images of the item, of a container in which the item is packed, or of a carrier transporting the item, wherein the one or more digital images are captured before, during, or after said shipment.

17. The method as recited in claim 1, wherein the contents of the memory device further comprise one or more digital images of the item showing the physical condition of the item upon receipt.

18. The method as recited in claim 1, wherein the memory device comprises an air testing device configured to test air samples for contaminants and to store test results in the contents of the memory device.

19. A system, comprising:
   a memory device, wherein the memory device stores information about an item, wherein the memory device accompanies the item during shipment from an origination to a final destination;
   a server connected to the memory device;
   wherein the server is configured to access the memory device via a network; and
   wherein the server is configured to:
      receive a request to ship the item and to insure the item during shipment from the origination to the final destination, wherein the request specifies the origination, the final destination, insurance information, and item information;
      prior to shipment of the item as a packaged item, and in response to receiving the request:
         automatically perform a search to select particular insurance for the packaged item according to one or more insurance criteria, wherein said performing the search to select particular insurance is based on the insurance information in the request to provide maximum insurance coverage for the packaged item during said shipment for the least cost;
         automatically perform a search to select a designated routing for the packaged item, wherein the search to select the designated routing comprises:
            determining an indirect route to be less costly than a more direct route, wherein the indirect route is longer than the more direct route,
            verifying that the indirect route meets a delivery deadline for the packaged item arriving at the final destination,
            selecting, based on said determining an indirect route to be less costly than a more direct route and based on said determining that both the indirect route and the more direct route are sufficient to meet the delivery deadline, the indirect route as a designated routing for the packaged item from the origination to the final destination;
         determine item information including one or more characteristics of the packaged item, the characteristics including one or more of a weight of the item, an image of the item, or a description of the item;
         determine insurer information including one or more terms of said particular insurance, the insurer information specifying the insurer selected to provide said particular insurance during said shipment;
         determine routing information specifying the designated routing for the packaged item, the routing information specifying segments of a multi-segment route from the origination to the final destination as specified in the request; and
         store the item information, the insurer information, and the routing information as contents of the memory device, wherein the memory device comprises an interface to update the contents according to current shipping conditions, via a remote device, before, during, and after said shipment;
      during the shipment of the packaged item and the memory device from the origination to the final destination, remotely update a data file stored on the memory device via the interface of the memory device;
      during the shipment of the packaged item and the memory device from the origination to the final destination, receive the updated data file subsequent to remotely updating the data file stored on the memory device; and
      during the shipment of the packaged item and the memory device from the origination to the final destination, receive updated information from the memory device based on a plurality of sensor measurements.

20. A non-transitory computer-readable storage medium which stores program instructions, wherein the program instructions are executable by a computer system to implement:
   receiving a request to ship an item and to insure the item during shipment from an origination to a final destination, wherein the request specifies the origination, the final destination, insurance information, and item information;
   prior to shipment of the item as a packaged item, and in response to said receiving the request:
      automatically performing a search to select particular insurance for the packaged item according to one or more insurance criteria, wherein said performing the search to select particular insurance is based on the insurance information in the request to provide maximum insurance coverage for the packaged item during shipment for the least cost;
      automatically performing a search to select a designated routing for the packaged item, wherein the search to select the designated routing comprises:
         determining an indirect route to be less costly than a more direct route, wherein the indirect route is longer than the more direct route,
         verifying that the indirect route meets a delivery deadline for the packaged item arriving at the final destination, and
         selecting, based on said determining an indirect route to be less costly than a more direct route and based on said determining that both the indirect route and the more direct route are sufficient to meet the delivery deadline, the indirect route as a designated routing for the packaged item from the origination to the final destination as specified in the request;
      determining item information including one or more characteristics of the packaged item, the characteristics including one or more of a weight of the item, an image of the item, or a description of the item;

determining insurer information including one or more terms of said particular insurance, the insurer information specifying the insurer selected to provide said particular insurance during said shipment;

determining routing information specifying the designated routing for the packaged item, the routing information specifying segments of a multi-segment route from the origination to the final destination; and storing the item information, the insurer information, and the routing information as contents of the memory device, wherein the memory device comprises an interface to read or to update the contents according to current shipping conditions, via a remote device, before, during, and after said shipment;

during the shipment of the packaged item and the memory device from the origination to the final destination, remotely updating, by the computer system, a data file stored on the memory device via the interface of the memory device;

during the shipment of the packaged item and the memory device from the origination to the final destination receiving, by the computer system, the updated data file subsequent to the computer system remotely updating the data file stored on the memory device; and during the shipment of the packaged item and the memory device from the origination to the final destination, receiving updated information from the memory device on a periodic basis.

\* \* \* \* \*